United States Patent
Ward et al.

(10) Patent No.: US 11,390,913 B2
(45) Date of Patent: Jul. 19, 2022

(54) SINGLE PRIMER TO DUAL PRIMER AMPLICON SWITCHING

(71) Applicant: SIGMA-ALDRICH CO. LLC, St. Louis, MO (US)

(72) Inventors: Brian W. Ward, St. Louis, MO (US); Carol A. Kreader, Kirkwood, MO (US); Jaime K. Robert, St. Louis, MO (US); Kenneth E. Heuermann, Kirkwood, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 425 days.

(21) Appl. No.: 16/334,343

(22) PCT Filed: Sep. 22, 2017

(86) PCT No.: PCT/US2017/052885
§ 371 (c)(1),
(2) Date: Mar. 18, 2019

(87) PCT Pub. No.: WO2018/057846
PCT Pub. Date: Mar. 29, 2018

(65) Prior Publication Data
US 2019/0211386 A1 Jul. 11, 2019

Related U.S. Application Data

(60) Provisional application No. 62/398,251, filed on Sep. 22, 2016.

(51) Int. Cl.
*C12Q 1/6853* (2018.01)
*C12Q 1/686* (2018.01)
*C12Q 1/6876* (2018.01)
*C40B 40/08* (2006.01)

(52) U.S. Cl.
CPC .......... *C12Q 1/6853* (2013.01); *C12Q 1/686* (2013.01); *C12Q 1/6876* (2013.01); *C40B 40/08* (2013.01)

(58) Field of Classification Search
None
See application file for complete search history.

(56) References Cited

U.S. PATENT DOCUMENTS

| 2003/0228620 A1 | 12/2003 | Du |
| 2010/0255546 A1 | 10/2010 | Uematsu et al. |

FOREIGN PATENT DOCUMENTS

| WO | 92/18521 A1 | 10/1992 |
| WO | 2005/060641 A2 | 7/2005 |
| WO | 2014/096394 A1 | 6/2014 |
| WO | 2015/117040 A1 | 8/2015 |
| WO | 2015/134488 A1 | 9/2015 |
| WO | 2016/154455 A1 | 9/2016 |
| WO | 2016/181128 A1 | 11/2016 |
| WO | 2018/057846 A1 | 3/2018 |

OTHER PUBLICATIONS

Zhang, et al., "CHO Glycosylation Mutants as Potential Host Cells to Produce Therapeutic Proteins with Enhanced Efficacy", Advances in Biochemical Engineering/Biotechnology, Nov. 10, 2012, vol. 131, pp. 63-87.
Buchman, et al., "Selective RNA Amplification: A Novel Method Using DUMP-containing Primers and Uracil DNA Glycosylase", Genome Research, 1993, pp. 28-31.
Fässler, et al., "Lack of β1 Integrin Gene in Embryonic Stem Cells Affects Morphology, Adhesion, and Migration But Not Integration into the Inner Cell Mass of Blastocysts", The Journal of Cell Biology, Mar. 1995, vol. 128, No. 5, pp. 979-988.
Jan, et al., "Characterization of a Chinese Hamster Ovary Cell Line Developed by Retroviral Insertional Mutagenesis That Is Resistant to Sindbis Virus Infection", Mar. 16, 1999, vol. 73, No. 6, pp. 4919-4924.
Lee, et al., "CRISPR/Cas9-mediated genome engineering of CHO cell factories: Application and perspectives", Biotechnology Journal, Jun. 9, 2015, vol. 10, No. 7, pp. 979-994.
Lee, et al., "Site-specific integration in CHO cells mediated by CRISPR/Cas9 and homology-directed DNA repair pathway", Scientific Reports, Feb. 25, 2015, vol. 5, pp. 1-11.
Lin, et al., "Chinese Hamster Ovary (CHO) Host Cell Engineering to Increase Sialylation of Recombinant Therapeutic Proteins by Modulating Sialyltransferase Expression", Biotechnology Progress, Jan. 2015, vol. 31, No. 2, pp. 334-346.
Mascarenhas, et al., "Genetic Engineering of CHO Cells for Viral Resistance to Minute Virus of Mice", Biotechnology and Bioengineering, vol. 114, No. 3, Oct. 12, 2016, pp. 576-588.
International Preliminary Report on Patentability received for PCT Application No. PCT/US2017/052885 dated Apr. 4, 2019, 7 pages.
International Search Report and Written Opinion received for PCT Application No. PCT/US2017/052885 dated Jan. 2, 2018, 10 pages.
International Preliminary Report on Patentability received for PCT Application No. PCT/US2018/015023, dated Aug. 8, 2019, 10 pages.
International Search Report and Written Opinion received for PCT Application No. PCT/US2018/015023, dated Jul. 6, 2018, 17 pages.
Rand, et al., "Headloop suppression PCR and its application to selective amplification of methylated DNA sequences", Nucleic Acids Research, Jul. 14, 2005, vol. 33, No. 14, pp. 1-11.
Rashtchian, et al., "Uracil DNA Glycosylase-Mediated Cloning of Polymerasechain Reaction-Amplified DNA: Application to genomic and cDNA cloning", Analytical Biochemistry, vol. 206, Issue 1, Oct. 1992, pp. 91-97.
Ronda, et al., "Accelerating Genome Editing in CHO Cells Using CRISPR Cas9 and CRISPy, a Web-Based Target Finding Tool", Biotechnology and Bioengineering, May 22, 2014, vol. 111, No. 8, pp. 1604-1616.

(Continued)

*Primary Examiner* — Samuel C Woolwine
*Assistant Examiner* — Carolyn L Greene
(74) *Attorney, Agent, or Firm* — Sigma-Aldrich Co. LLC

(57) ABSTRACT

Methods for primer switching during amplification reactions are provided. In particular, methods are provided for converting single primer PCR amplicons to dual primer PCR amplicons.

20 Claims, 23 Drawing Sheets
(20 of 23 Drawing Sheet(s) Filed in Color)
Specification includes a Sequence Listing.

(56) References Cited

OTHER PUBLICATIONS

Rubin, et al., "Cellular genetics of host susceptibility and resistance to virus infection", Critical Reviews in Eukaryotic Gene Expression, vol. 16, No. 2, Jan. 1, 2006, pp. 155-170.

Sealover, et al., "Engineering Chinese Hamster Ovary (CHO) Cells for Producing Recombinant Proteins with Simple Glycoforms by Zinc-Finger Nuclease (ZFN)—Mediated Gene Knockout of Mannosyl (alpha-1,3-)-glycoprotein beta-1,2-N-acetylglucosaminyltransferase (Mgat1)", Jun. 15, 2013, pp. 24-32.

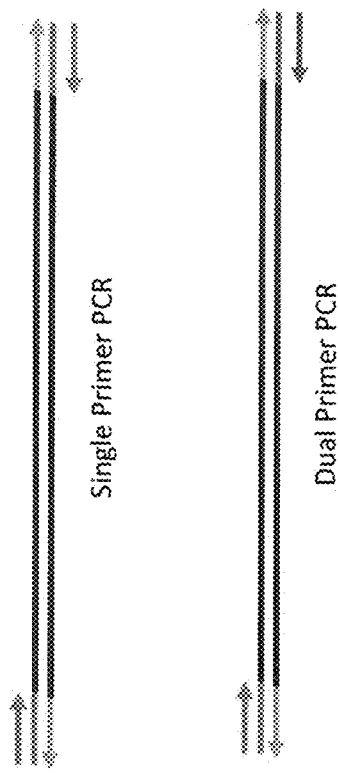

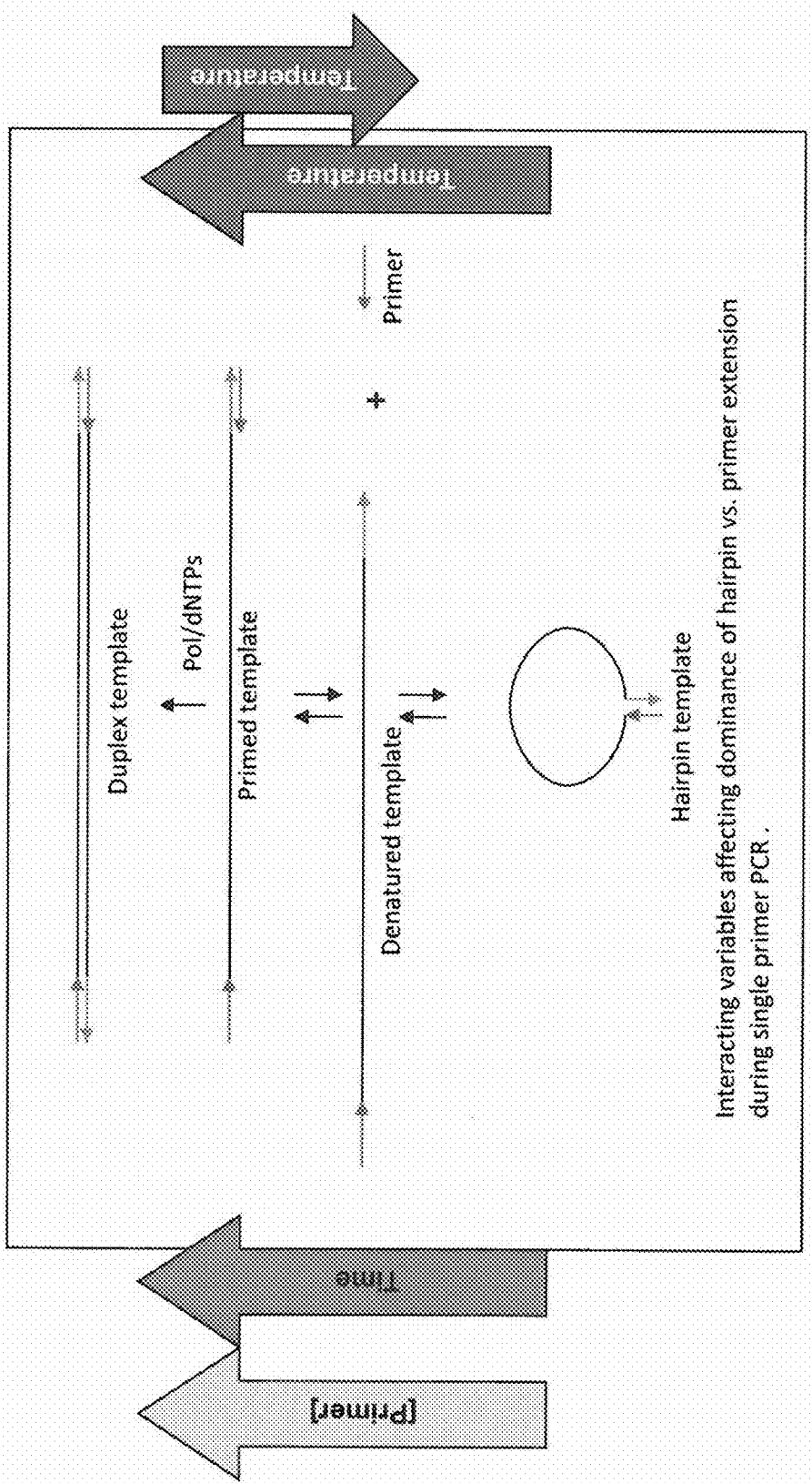
Figure 2. By definition, single primer PCR produces amplicons that are 5'-3' complimentary.

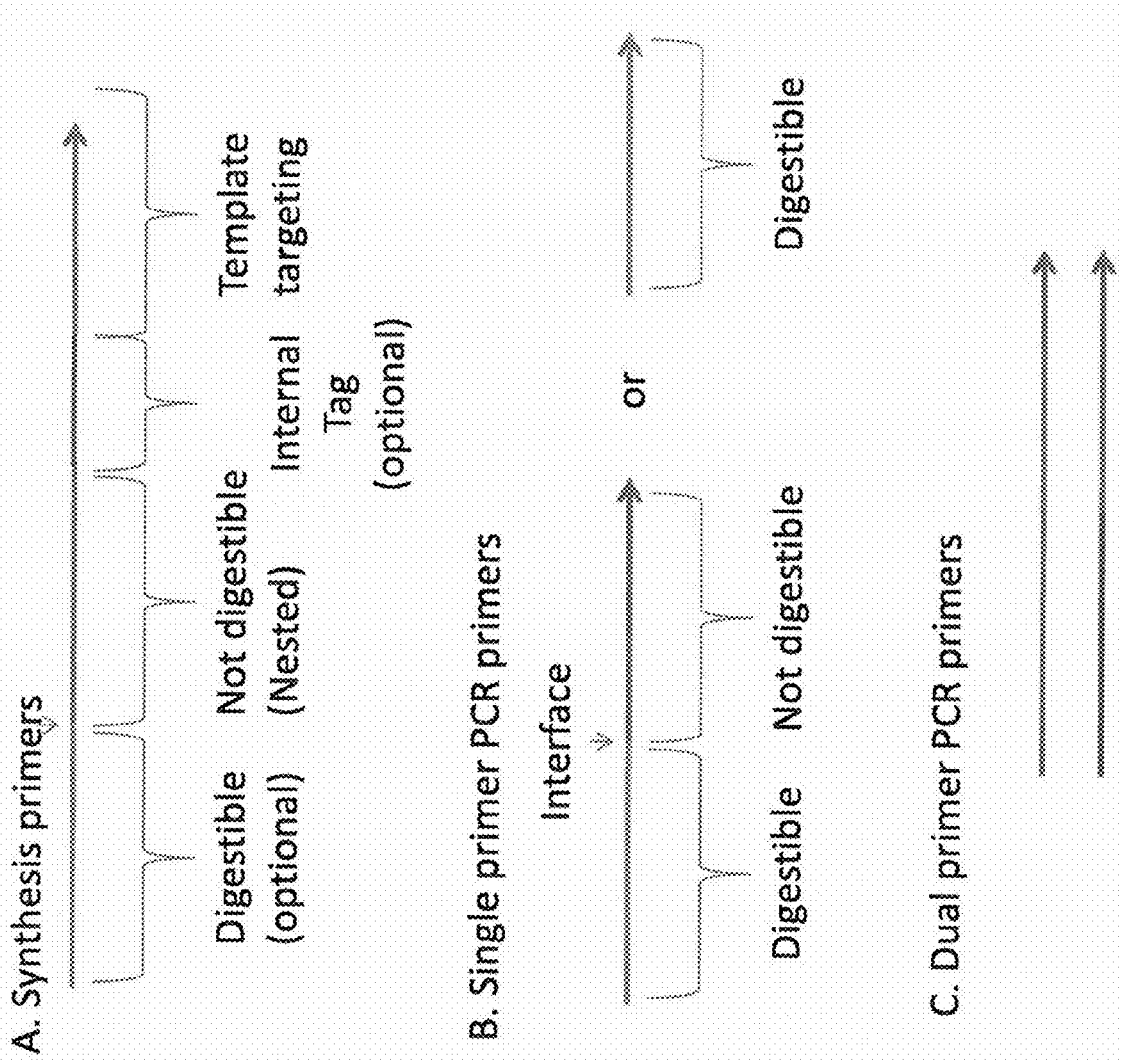
Figure 3. Primer designs (colors indicate sequence homology)

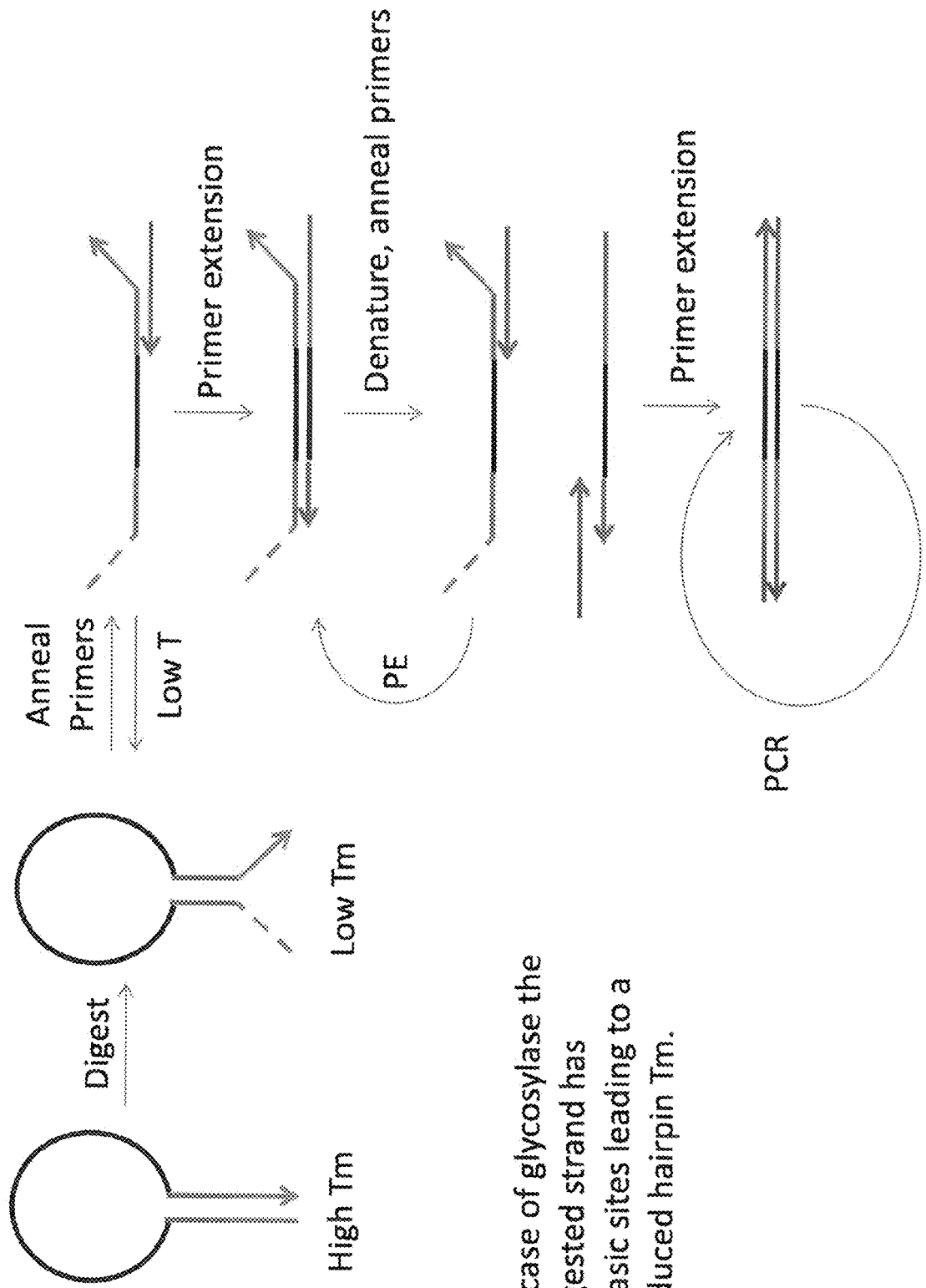

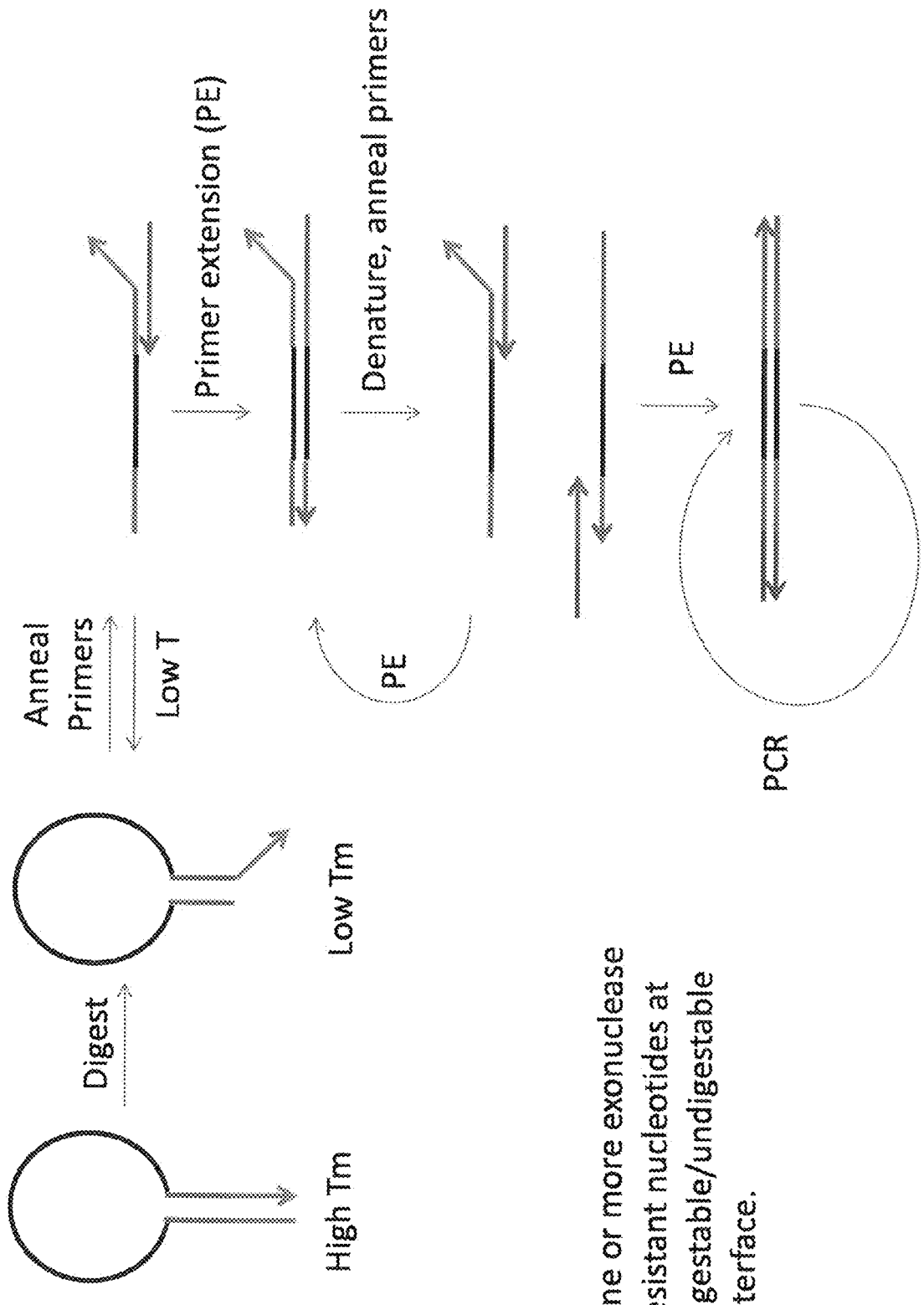

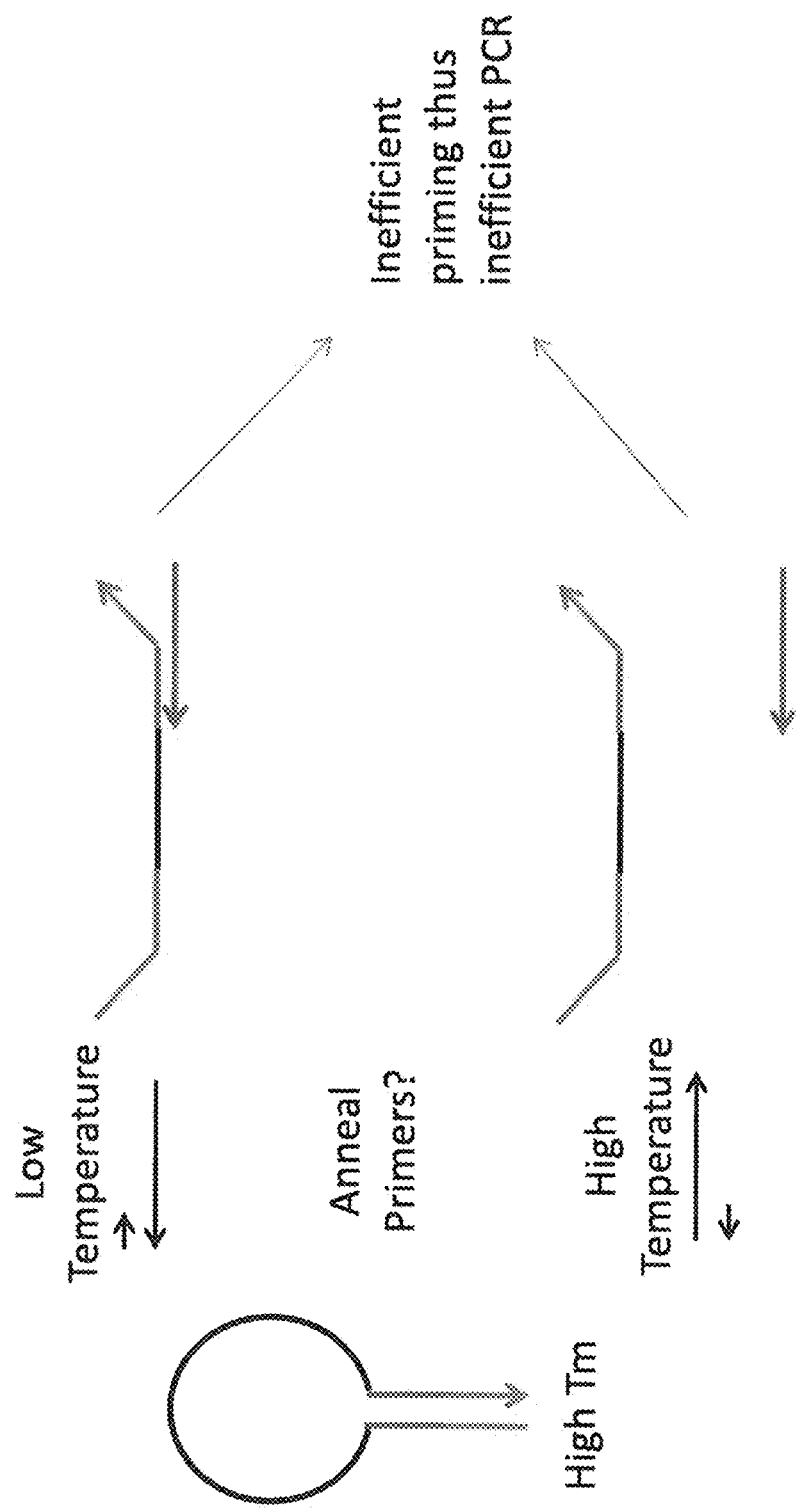
Figure 6. No digestion annealing

Figure 7. Uracil example primers

PCR1 single primer PCR     UGGUUGUGUUUGCTCTTTCCGATCT    Tm = 70°C
                                             Tm = 44°C PCR2 Dual primers Short
TCAGACGTGTGCTCTTCCGATCT
CCTACACGACGCTCTTCCGATCT Long
AATGATACGGCGACCACCGAGATCTACACTCTTTCCCTACACGACGCTCTTCCGATCT
CAAGCAGAAGACGGCATACGAGATATTACTCGGTGACTGGAGTTCAGACGTGTGCTCTTCCGATCT

Figure 8. Exonuclease example primers

PCR1 single primer PCR    TGGTTGTGTTTGCTCTTCCGATCT

PCR2 Dual primers

↑
1 to n
nuclease resistant
linkages beginning at
5' end.

Short
TCAGACGTGTGCTCTTCCGATCT
CCTACACGACGCTCTTCCGATCT

Long
AATGATACGGGCGACCACCGAGATCTACACTCTTTCCCTACACGACGCTCTTCCGATCT
CAAGCAGAAGACGGCATACGAGATATTACTCGGTGACTGGAGTTCAGACGTGTGCTCTTCCGATCT

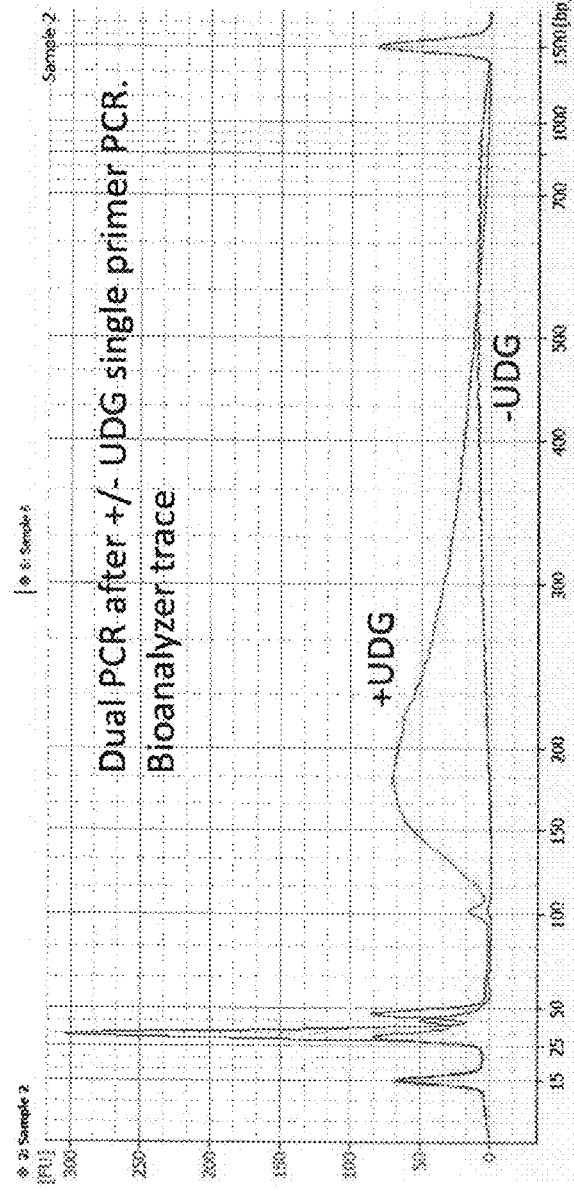

Figure 9. With vs. without digestion dual primer PCR

Dual PCR after +/- UDG single primer PCR. Bioanalyzer trace 10 ng gDNA > Whole Genome Amplification (single primer PCR) > Dual primer PCR +/- UgG WGA primers
Library- UGGUUGUGUUUGCTCTTCCGATCT-9 quasi degenerate bases
Single primer amplification- UGGUUGUGUUUGCTCTTCCGATCT Dual primers
Forward- TCAGACGTGTGCTCTTCCGATCT
Reverse- CCTACACGACGCTCTTCCGATCT Cycling parameters
WGA- as Sigma Seqxe
Dual primer (10-50% v/v WGA in PCR)
+/- 10% v/v UDG, 30 min @ 37°C
2 cycles 94°C/30 sec, 50°C/10 min
X cycles 94°C/30 sec, 70°C/1 min
(x = to SYBR Green plateau)

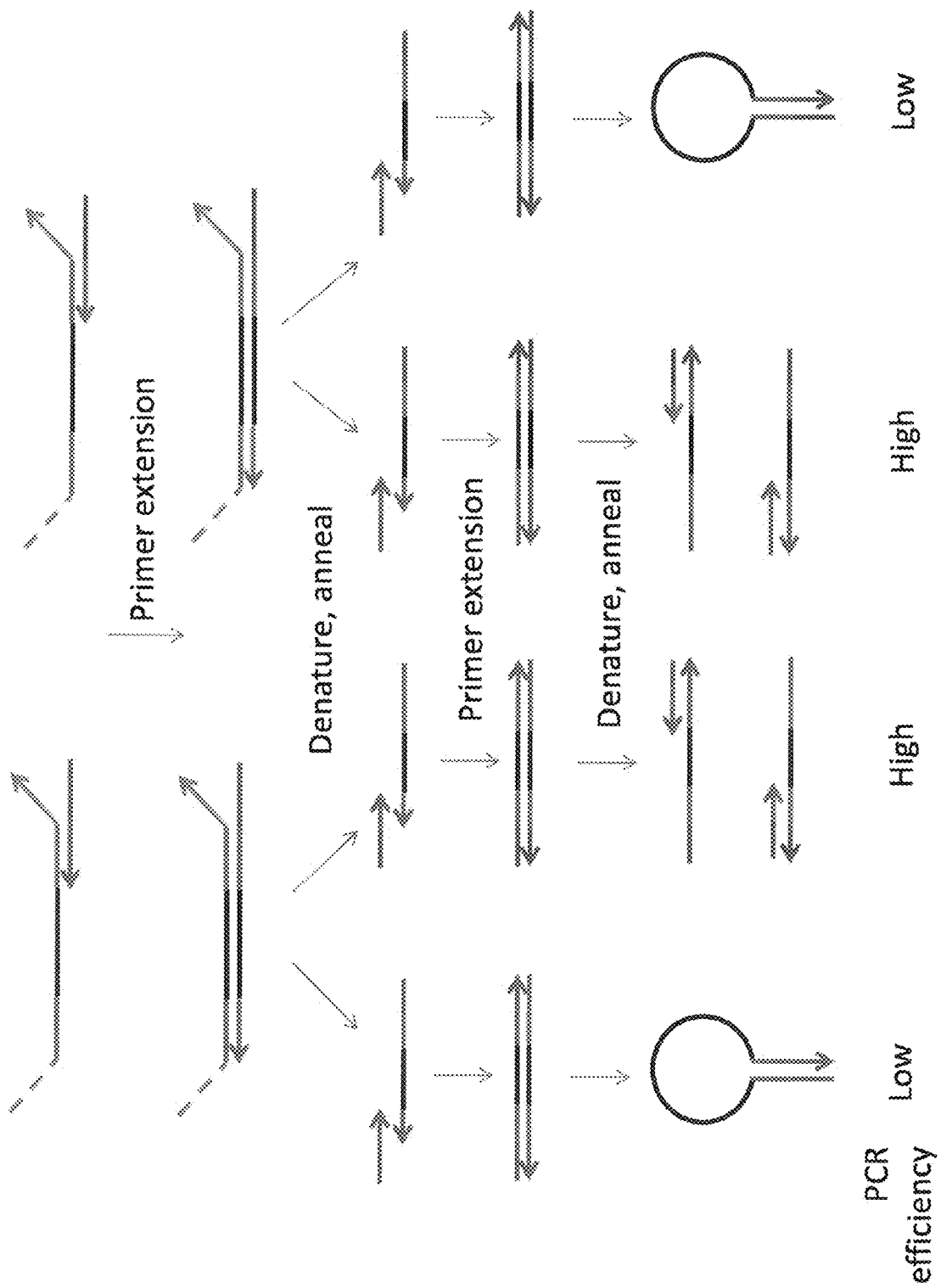

Figure 11. WGA as figure 9, UDG then amplifications with possible combinations of primers.
PCR monitored by SYBR Green. For, Rev + WGA and WGA (red) alone would not be present in preferred method. Approximately 8 to 9 cycle difference between dual For/Ref vs. For or Rev alone Cts indicate <1% of amplification product has complementary 5'-3' ends (i.e. $2^{-(8 \text{ to } 9)} < 0.01$). Note also difference in product distributions. Hairpin stability is inversely proportional to amplicon length. For and Rev primer amplications selectively amplify longer template molecules.

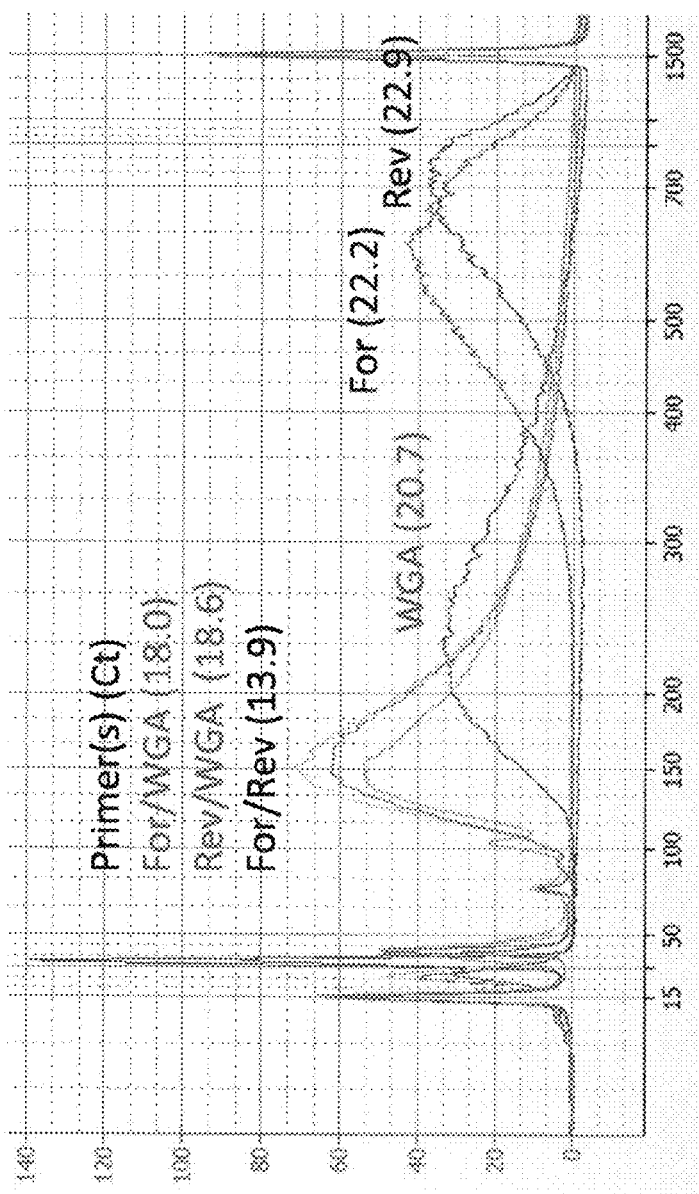

Figure 12. Short vs. long dual primer PCRs
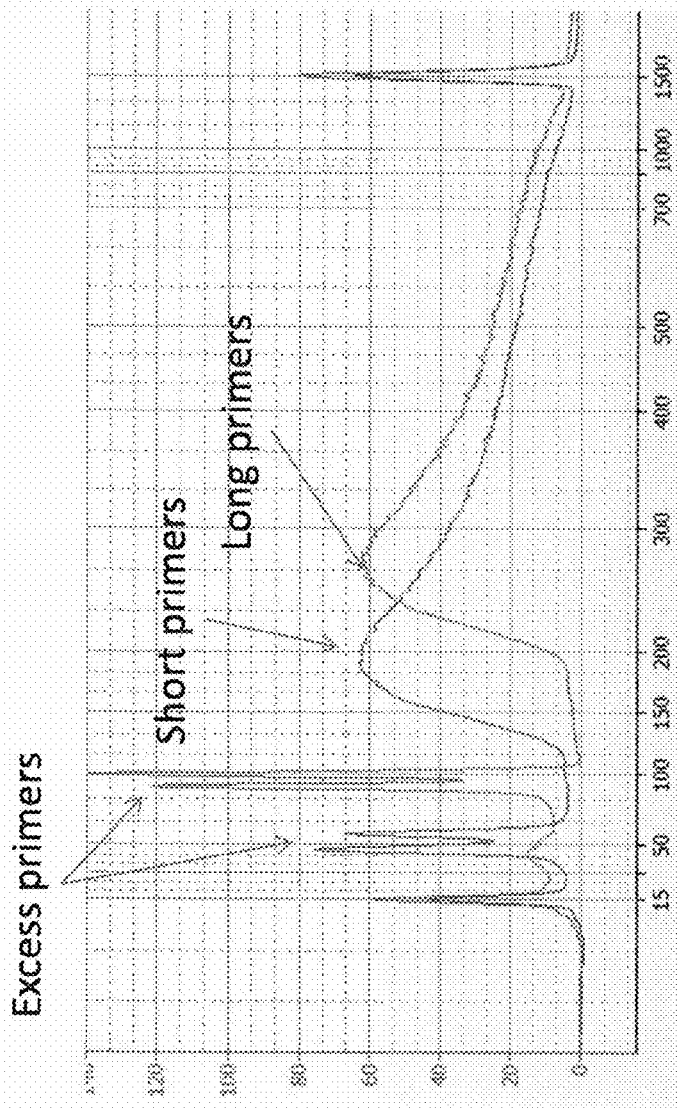
Short primers
TCAGACGTGTGCTCTTCCGATCT
CCTACACGACGCTCTTCCGATCT
Long primers
AATGATACGGCGACCACCGAGATCTACACTATAGCCTACACTCTTTCCCTACACGACGCTCTTCCGATCT
CAAGCAGAAGACGGCATACGAGATATTACTCGGTGACTGGAGTTCAGACGTGTGCTCTTCCGATCT

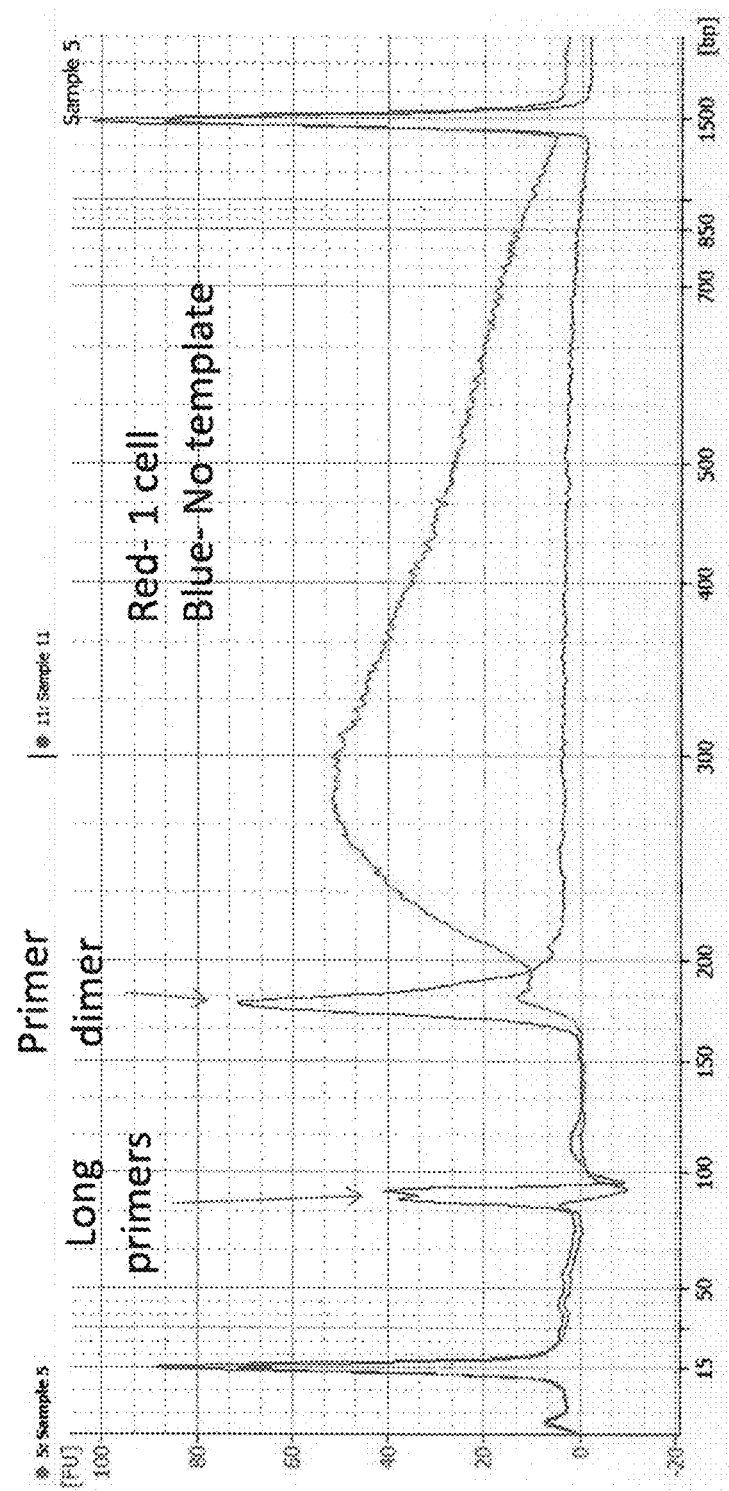
Figure 13. Single cell amplification- 22 cycles WGA, 9 cycles dual primer PCR (10% v/v UDG). Demonstrates usefulness with vanishingly small quantities of nucleic acids.

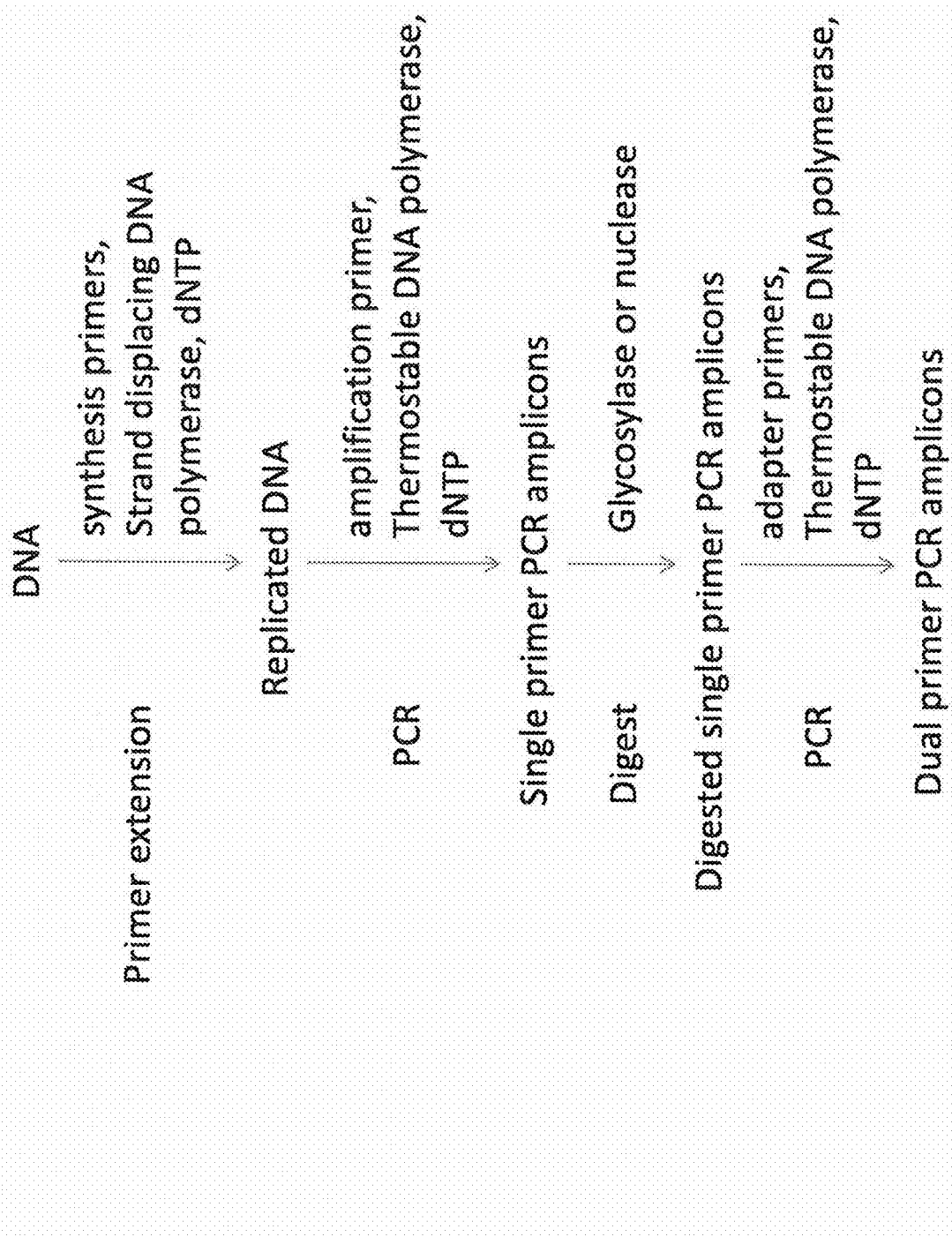
Figure 14. DNA workflow

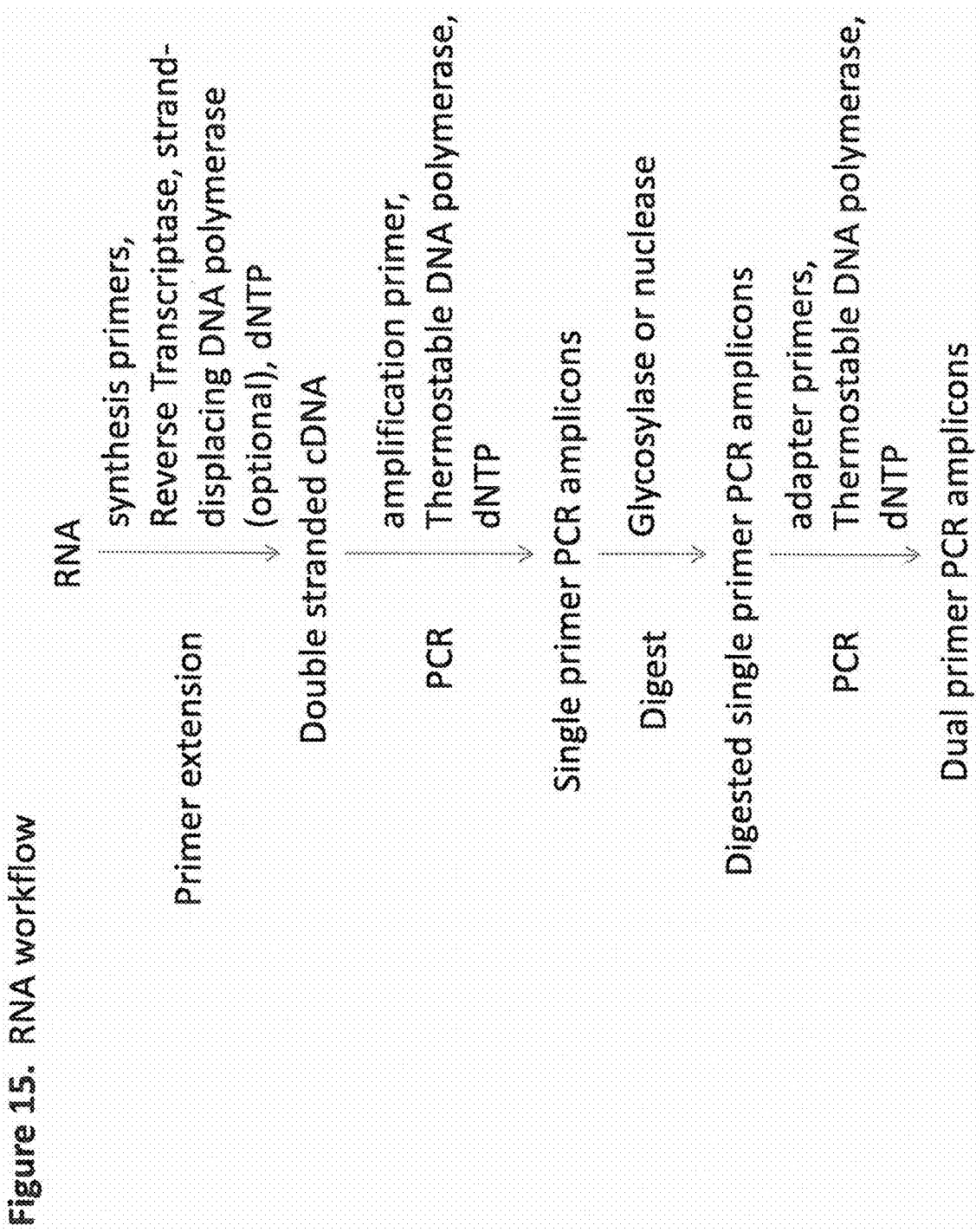
Figure 15. RNA workflow

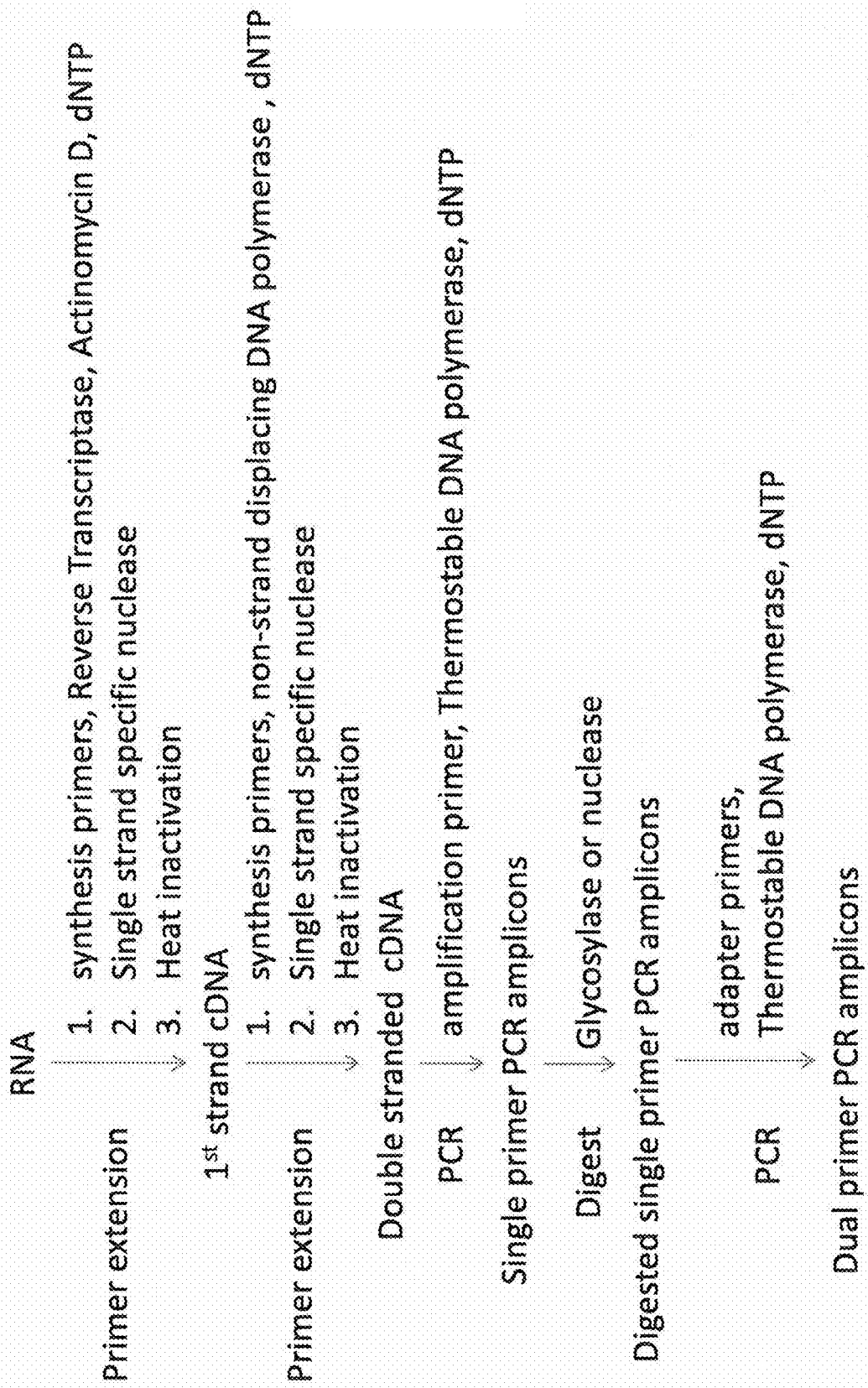
Figure 16. Directional RNA workflow

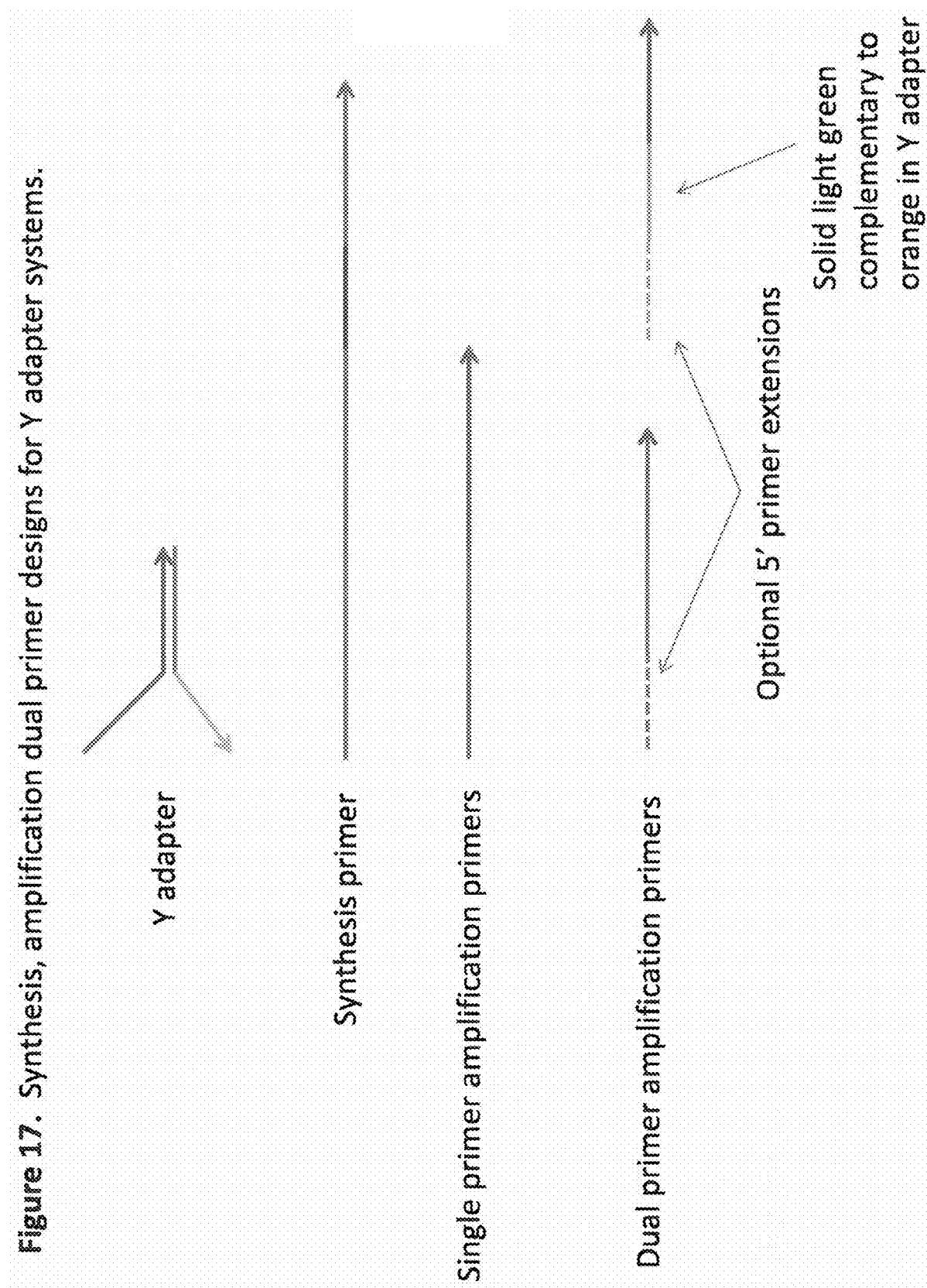

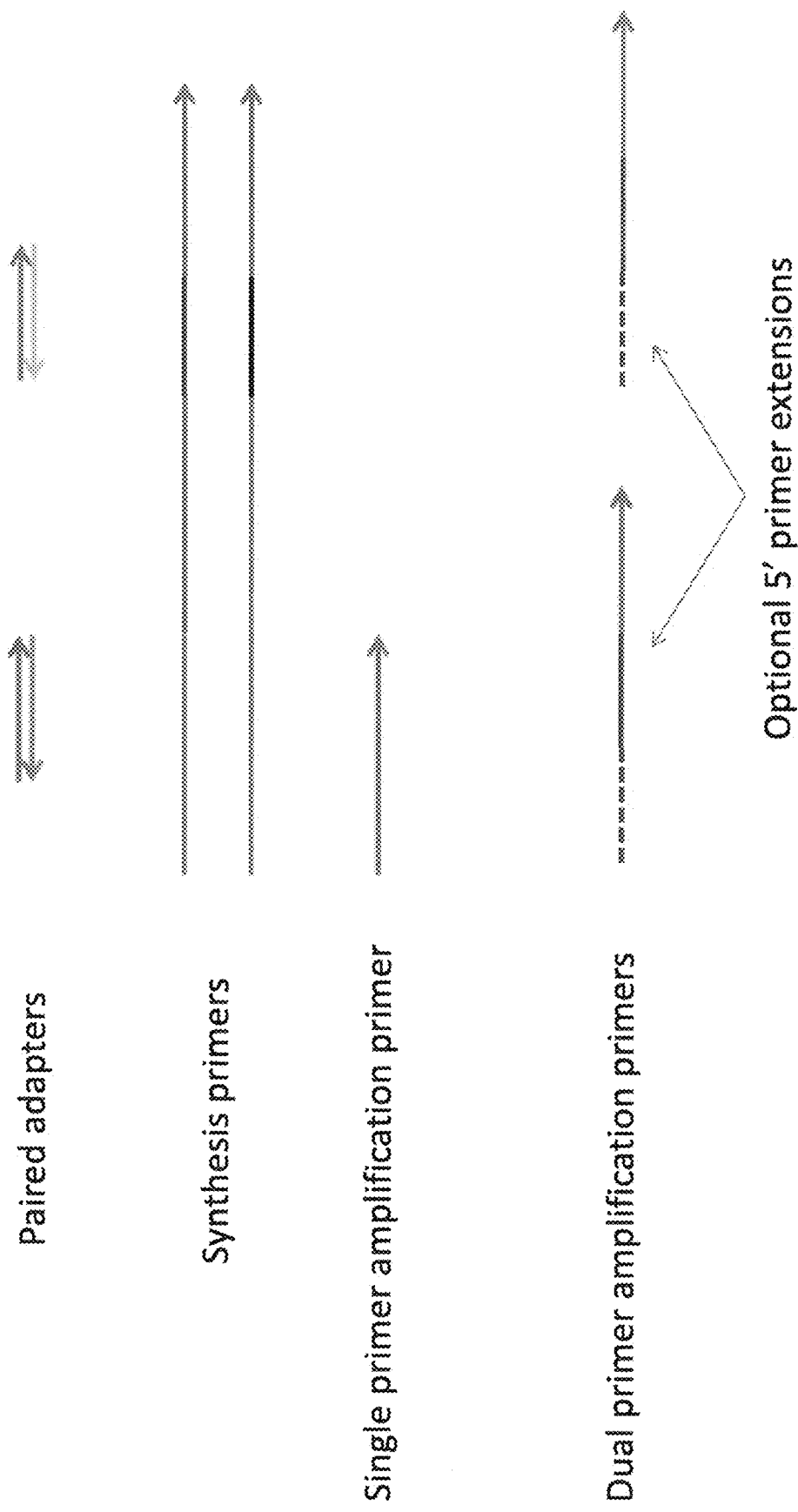
Figure 18. Synthesis, amplification and dual primer design for paired adapter systems.

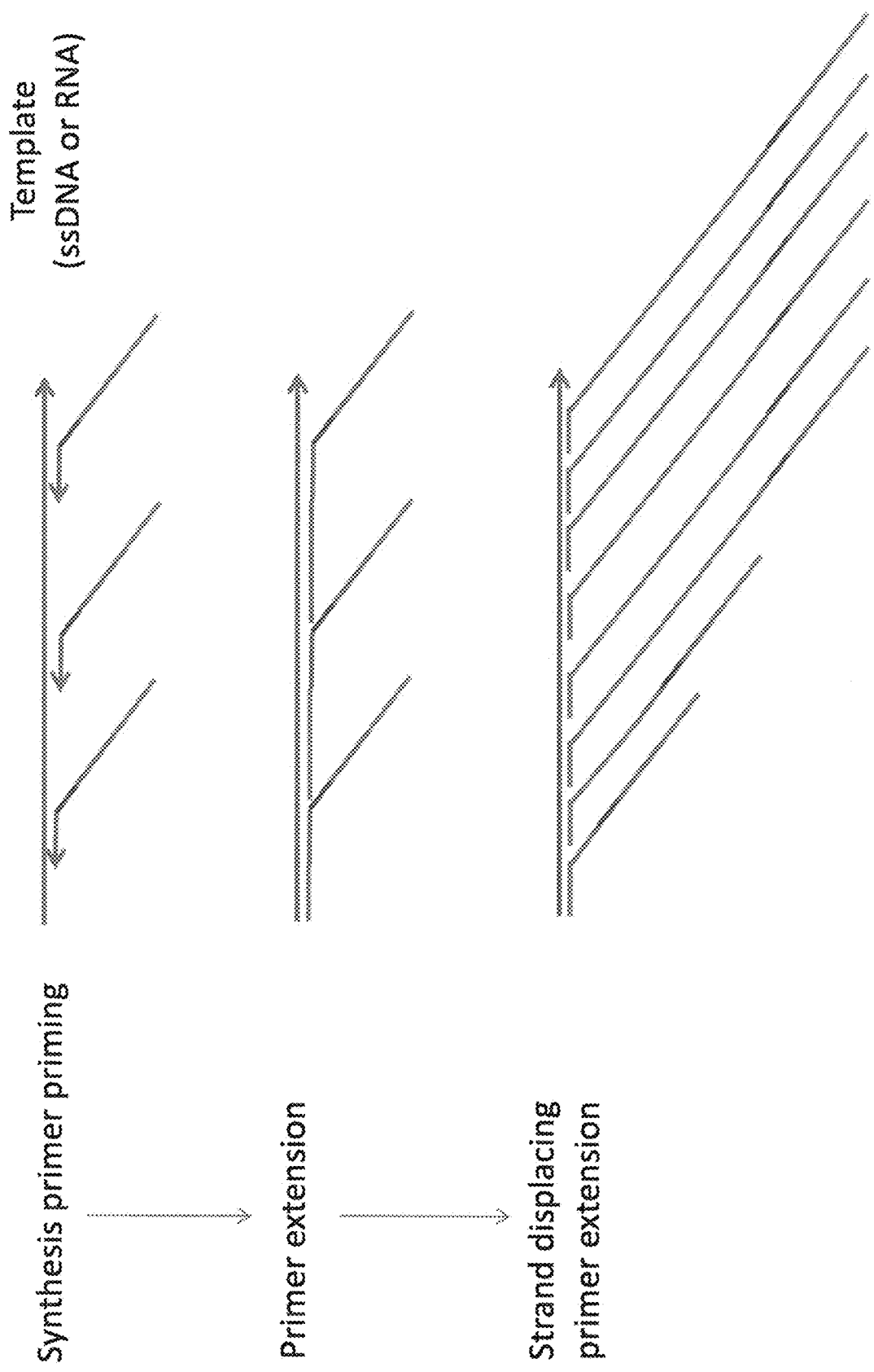

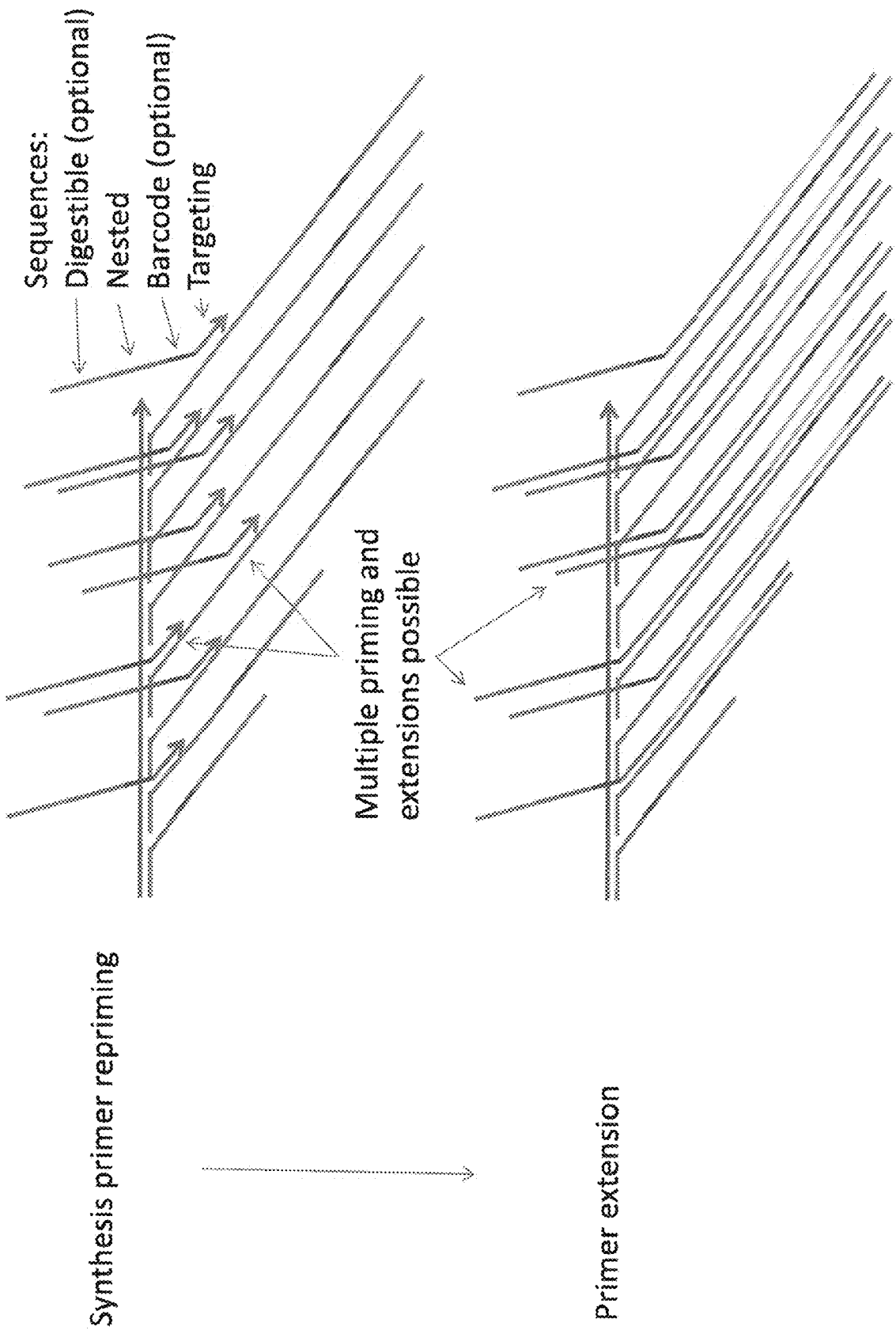
Figure 20. Non-directional second strand synthesis

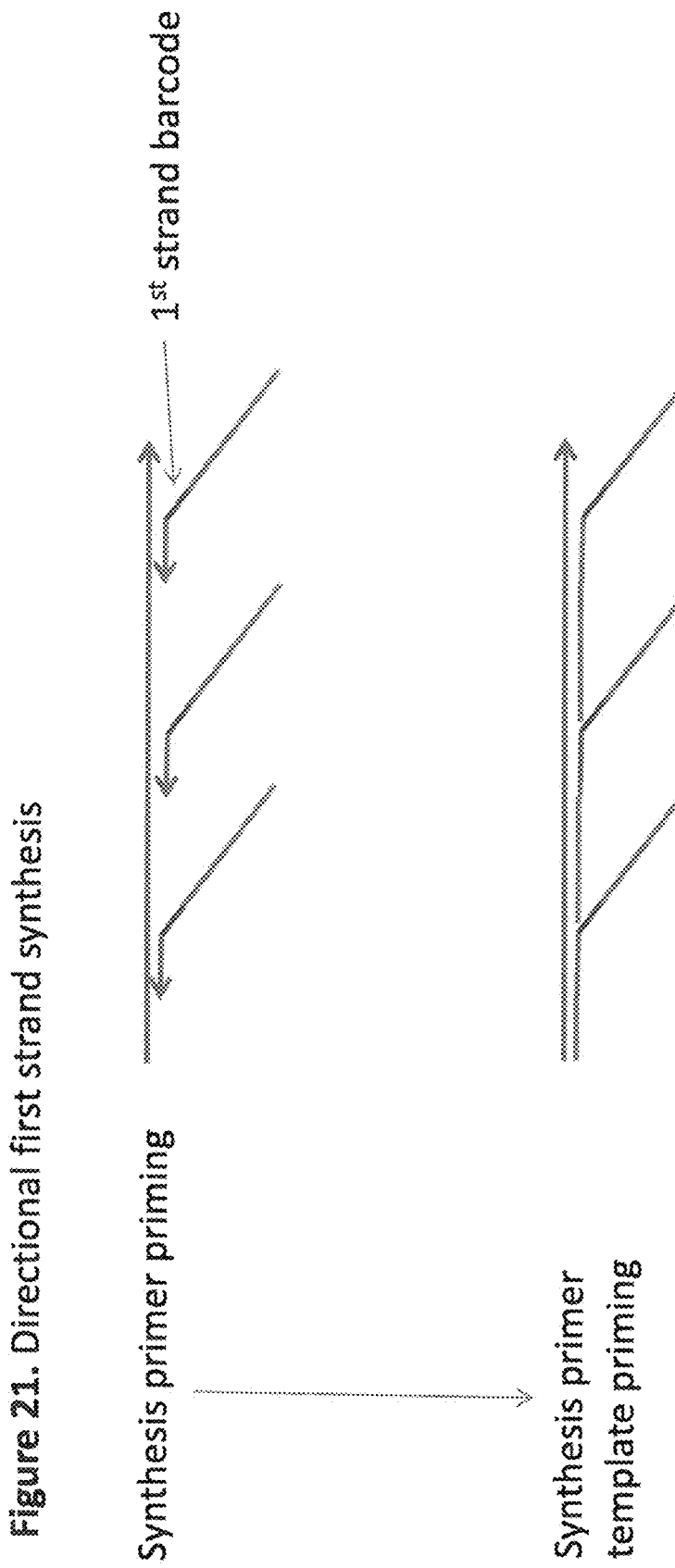
Figure 21. Directional first strand synthesis

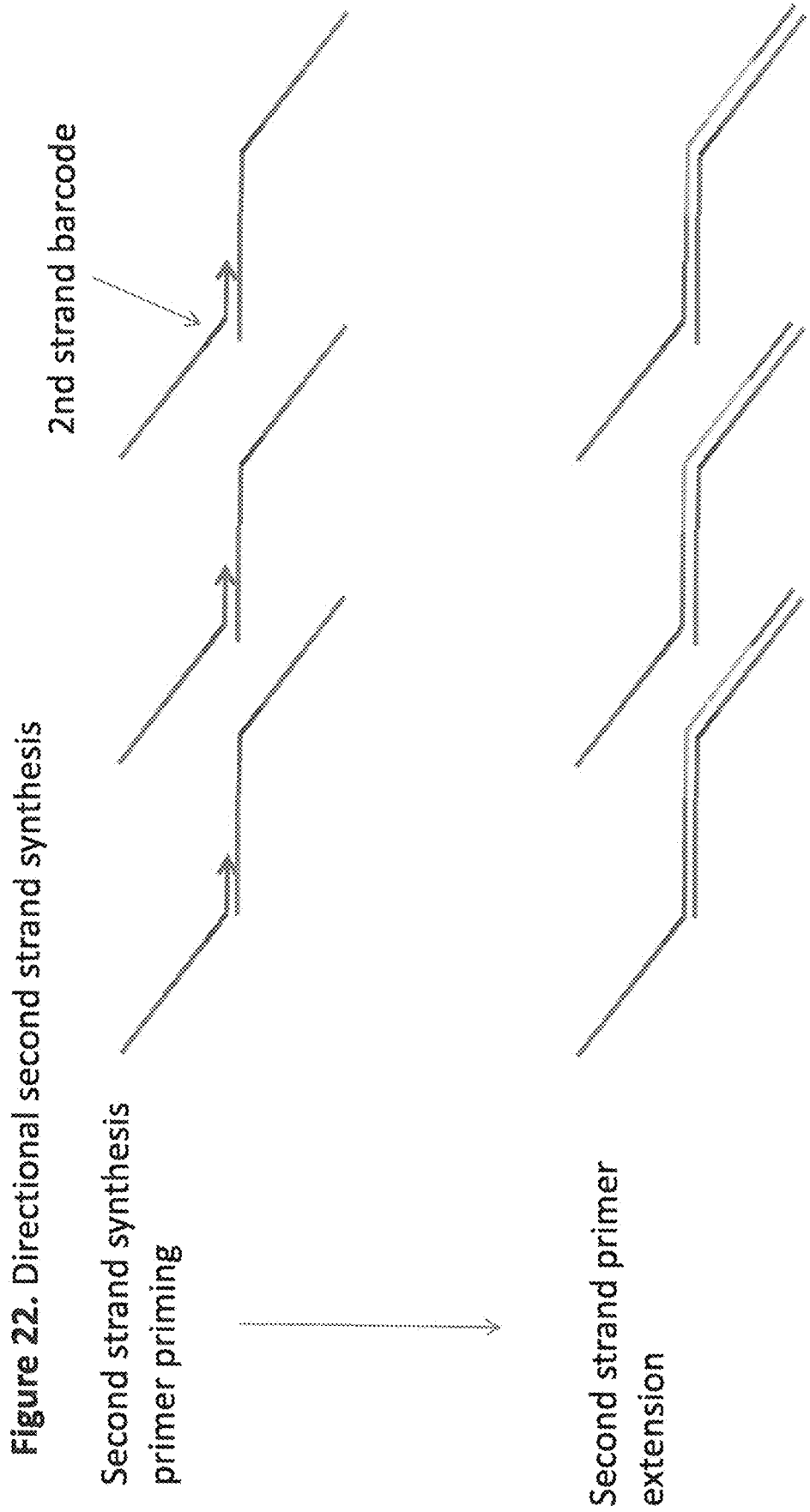
Figure 22. Directional second strand synthesis

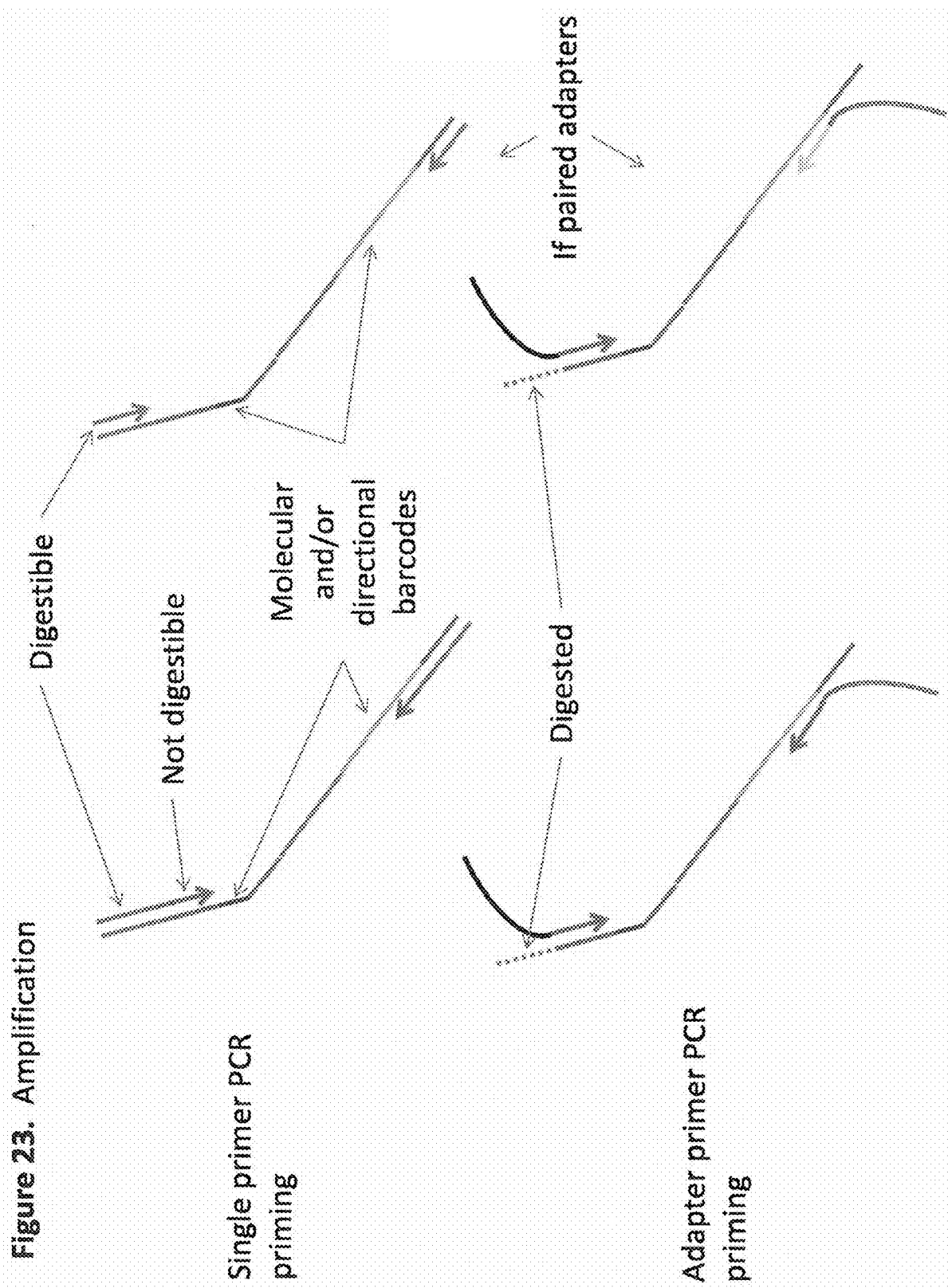

SEQUENCE LISTING

```
<160> NUMBER OF SEQ ID NOS: 21

<210> SEQ ID NO 1
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"
<220> FEATURE:
<221> NAME/KEY: modified_base
<222> LOCATION: (26)..(28)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (32)..(32)
<223> OTHER INFORMATION: a, c, t, g, unknown or other

<400> SEQUENCE: 1
ugguuguguu ugctcttccg atctknnnkn knk                             33

<210> SEQ ID NO 2
<211> LENGTH: 24
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"

<400> SEQUENCE: 2
ugguuguguu ugctcttccg atct                                            24

<210> SEQ ID NO 3
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
tcagacgtgt gctcttccga tct                                             23

<210> SEQ ID NO 4
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
cctacacgac gctcttccga tct                                             23

<210> SEQ ID NO 5
<211> LENGTH: 70
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
aatgatacgg cgaccaccga gatctacact atagcctaca ctctttccct acacgacgct     60
cttccgatct                                                            70

<210> SEQ ID NO 6
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
caagcagaag acggcatacg agatattact cggtgactgg agttcagacg tgtgctcttc     60
cgatct                                                                66

<210> SEQ ID NO 7
<211> LENGTH: 40
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"
<220> FEATURE:
<221> NAME/KEY: modified_base
<222> LOCATION: (33)..(35)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other

<400> SEQUENCE: 7
gguuguguuu gctcttccga tctctaacta cknnnknknk                                40

<210> SEQ ID NO 8
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"
<220> FEATURE:
<221> NAME/KEY: modified_base
<222> LOCATION: (32)..(34)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other

<400> SEQUENCE: 8
gguuguguuu gctcttccga tctctaacta cnnnknkknk                                40

<210> SEQ ID NO 9
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"
<220> FEATURE:
<221> NAME/KEY: modified_base
<222> LOCATION: (32)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
```

```
<220> FEATURE:
<221> NAME/KEY: modified_base
<222> LOCATION: (37)..(38)
<223> OTHER INFORMATION: a, c, t, g, unknown or other

<400> SEQUENCE: 9
gguuguguuu gctcttccga tctctaacta cnknnknnkk                    40

<210> SEQ ID NO 10
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"
<220> FEATURE:
<221> NAME/KEY: modified_base
<222> LOCATION: (47)..(47)
<223> OTHER INFORMATION: a, c, t, g, unknown or other

<400> SEQUENCE: 10
gguuguguuu gctcttccga tctctaacta ctttttttttt tttttvn           47

<210> SEQ ID NO 11
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"
<220> FEATURE:
<221> NAME/KEY: modified_base
<222> LOCATION: (34)..(36)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other

<400> SEQUENCE: 11
gguuguguuu gctcttccga tctaagcctc gtknnnknkn k                  41

<210> SEQ ID NO 12
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"
<220> FEATURE:
<221> NAME/KEY: modified_base
<222> LOCATION: (33)..(35)
<223> OTHER INFORMATION: a, c, t, g, unknown or other
```

<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other

<400> SEQUENCE: 12
gguuguguuu gctcttccga tctaagcctc gtnnnknkkn k         41

<210> SEQ ID NO 13
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (38)..(39)
<223> OTHER INFORMATION: a, c, t, g, unknown or other

<400> SEQUENCE: 13
gguuguguuu gctcttccga tctaagcctc gtnknnknnk k         41

<210> SEQ ID NO 14
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"
<220> FEATURE:
<221> NAME/KEY: modified_base
<222> LOCATION: (48)..(48)
<223> OTHER INFORMATION: a, c, t, g, unknown or other

<400> SEQUENCE: 14
gguuguguuu gctcttccga tctaagcctc gttttttttt tttttvn    48

<210> SEQ ID NO 15
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"

```
<400> SEQUENCE: 15
gguuguguuu gctcttccga tct                                        23

<210> SEQ ID NO 16
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"

<400> SEQUENCE: 16
gguuguguuu gctcttccga tctctaac                                   28

<210> SEQ ID NO 17
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"

<400> SEQUENCE: 17
gguuguguuu gctcttccga tctgat                                     26

<210> SEQ ID NO 18
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"

<400> SEQUENCE: 18
gguuguguuu gctcttccga tctagc                                     26

<210> SEQ ID NO 19
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: source
<223> OTHER INFORMATION: /note="Description of Combined DNA/RNA
      Molecule: Synthetic primer"

<400> SEQUENCE: 19
gguuguguuu gctcttccga tcttc                                      25
```

```
<210> SEQ ID NO 20
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (16)..(16)
<223> OTHER INFORMATION: a, c, t, g, unknown or other

<400> SEQUENCE: 20
tttttttttt ttttvn                                                    16

<210> SEQ ID NO 21
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
tggttgtgtt tgctcttccg atct                                           24
```

SINGLE PRIMER TO DUAL PRIMER AMPLICON SWITCHING

CROSS-REFERENCE TO RELATED APPLICATIONS

This application is a U.S. National Stage Application of PCT International Application No. PCT/US2017/052885, filed Sep. 22, 2017, which claims priority to U.S. Provisional Application Ser. No. 62/398,251, filed Sep. 22, 2016, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 14, 2017, is named P16-221PCT-_SL.txt and is 9,240 bytes in size.

FIELD OF THE DISCLOSURE

The present disclosure relates to methods for switching amplicon ends during amplification reactions. In particular, it relates to converting single primer PCR amplicons to dual primer PCR amplicons.

BACKGROUND

Amplification reactions, such as polymerase chain reaction (PCR), are widely used in many applications. For example, DNA or RNA can be amplified for preparing libraries for DNA sequencing (e.g., next generation sequencing). Whole genome amplification (WGA) or whole transcriptome amplification (WTA) comprises single primer PCR which may be directly incompatible to applications requiring dual primer generated amplicons. This is routinely accomplished by ligating adapters directly to WGA or WTA amplicons or after excision of WGA/WTA primer sequences. There is a need for a quick and efficient means for switching primers during PCR.

The general workflow for preparing libraries for next generation sequencing includes template fragmentation, end repair, adapter ligation and PCR amplification. Critical to successful amplification is ligating adapter to both ends of a DNA fragment. Ligation is typically non-quantitative thus this workflow becomes difficult when vanishingly low quantities of nucleic acid are being sequenced. These methods typically require two or more purification steps for adapter removal (prior to amplification), potentially affecting post-amplification library representation.

Another generally high yielding option to introduce adapter sequence is by primer extension. For WGA/WTA this involves extending tailed degenerate or poly-A primers, in the case of some RNA species, hybridized to template. Primer dimer amplification is generally the most prevalent product when using distinct forward and reverse tails 5' of degenerate ends. Primer dimer is effectively minimized when using a single common priming sequence 5' of the degenerate bases. This is due to formation of short stable primer dimer hairpins that are very inefficiently amplified. Longer amplicons also form hairpins but are much less stable than the small primer-primer "lollipop" primer dimer structures (much smaller loop relative to stem) allowing for more efficient amplification.

With nucleic acid libraries, it is often important to know the "directionality" or orientation of library amplicons relative to their templates. One primer extension-based WTA method designed to directionally amplify low quantities of RNA involves the use of "template switching", not to be confused with the "primer switching" concept described herein. Another directional RNA amplification method employs ligation (and multiple purification steps). This approach relies upon dUTP incorporation during second strand cDNA synthesis, with subsequent ligation of sequencing adapters and uracil DNA glycosylase digestion of the second strand, followed further by dual primer PCR amplification of the resulting anti-sense cDNA library.

There is a need, therefore, for nucleic acid amplification methods that are applicable for low input quantities and/or low quality (FFPE), devoid of purification steps, and capable of indicating amplification product strandedness.

SUMMARY

Among the various aspects of the present disclosure is the provision of a method for converting a single primer PCR amplicon to a dual primer PCR amplicon. The method comprises treating the single primer PCR amplicon with an enzyme capable of digesting a 5' portion of the single primer PCR amplicon to form a digested amplicon, and amplifying the digested amplicon with a pair of primers having homology to an undigested portion of the digested amplicon, thereby forming the dual primer PCR amplicon.

Other aspects and iterations of the present disclosure include amplification from DNA or RNA. RNA has the option of directional and non-directional amplification. Methods can also be applied to multiplex amplification wherein the 3'degeneracy of the first primer ends is reduced to include a predetermined set of target amplicons instead of a fully or partially degenerate mixture. In all cases primer dimer amplification is suppressed by using a single PCR primer for an initial amplification.

Amplification of DNA entails synthesis of a replication library using template targeting primers 5' tailed with the single PCR primer sequence followed by PCR. Template targeting primers are annealed, extended using a strand displacing DNA polymerase then PCR amplified using the single PCR primer. Non-directional RNA amplification is performed similarly. Template targeting primers are annealed, extended using a strand displacing reverse transcriptase/DNA polymerase then PCR amplified using the single PCR primer (see FIGS. 4 and 5). Directional RNA amplification is accomplished by sequential first then second strand synthesis under non-strand displacing conditions. Directionality is monitored using directional tags engineered into the first and/or second strand template targeting primers (see FIGS. 21, 22, and 23). Molecular identity can similarly be monitored by tags engineered into the synthesis primer(s).

Conversion of single primer to dual primer amplicons requires hybridization of the dual primers to the single primer amplicon. When the dual primer is homologous to some but not all of the single primer the stability of inter and intra molecular amplicon hybrids effectively competes with dual primer hybridization (see FIG. 6). This effect is mitigated by engineering digestible or exonuclease resistant residues into the single amplification primer and optionally the sequence of the template targeting primers. Digestion reduces the stability of inter and intramolecular amplicon hybrids allowing efficient priming by the dual primers. Digestible residues include glycolase sensitive and nuclease resistant moieties well known in the art. A preferred embodiment pairs uracil residues with uracil DNA glycosylase to destabilize inter/intrastrand hybridization (see FIGS. 4 and 5).

The workflow can be generically summarized: primer extend hybridized first then second (if applicable) primers, amplify with single primer, digest 5' amplicon ends then amplify with dual primers. Dual primer amplicons are suitable for downstream applications such as but not limited to next generation sequencing. First and second primers will generally be a plurality of primers ranging from 3' random primer to a pool of directed primer pairs resulting in production of several to millions of unique amplicons (see FIGS. 14, 15, and 16).

A further aspect of the present disclosure provides a plurality of artificial oligonucleotides comprising (a) a plurality of oligonucleotides in which each comprises (5' to 3') a 5' sequence comprising; a 5' sequence optionally comprising at least one digestible or nuclease resistant residue; nested sequence having homology to an adapter primer sequence; an optional internal tag sequence comprising for directional or and/or molecular ID amplification a tag sequence, and a 3' sequence comprising a random, semi-random or pooled target specific sequences (see FIG. 3A). For directional amplification a plurality of second oligonucleotides in which each comprises (5' to 3') a 5' sequence comprising optionally at least one digestible or nuclease resistant residue; a nested sequence having homology to an adapter primer sequence, an optional internal tag sequence comprising a second tag sequence, and a 3' sequence comprising a random, semi-random or pooled target specific sequences, provided that for directional amplification either one or both of the pluralities of first and second oligonucleotides comprises the first and/or second tag sequence. No matter whether starting from DNA or RNA and directional or non-directional, a further aspect is an artificial oligonucleotide comprising at least one digestible or nuclease resistant residue (see FIG. 3B).

Still another aspect of the present disclosure encompasses kits for amplifying DNA or RNA. The kit comprises (a) optionally a plurality of synthesis primers in which each synthesis primer comprises a 5' sequence optionally comprising at least one digestible or nuclease resistant residue, a nested sequence having homology to an adapter primer sequence, an optional internal tag sequence, and a random or semi-random 3' sequence; and optionally (b) a plurality of second synthesis primers in which each second synthesis primer comprises a 5' sequence comprising optionally at least one digestible or nuclease resistant residue, a nested sequence having complementarity to an adapter sequence, an optional internal tag sequence comprising a second tag sequence, and a random or semi-random 3' sequence. For directional amplification, either one or both of the pluralities of first and second synthesis primers comprises the first and/or second tag sequence. Additionally, kits comprise of at least one amplification primer comprising the 5' sequence of the synthesis primers and at least one digestible or nuclease resistant residue. The digestible residue is uracil in a preferred embodiment.

Other aspects and iterations of the present disclosure are detailed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 illustrates primer and template sequences of single vs dual primer PCR.

FIG. 2 diagrams the variables that affect the dominance of hairpin template formation versus primer extension during single primer PCR.

FIG. 3 Illustrates primer designs. A. Synthesis primers. Tags can be for directionality, molecular barcoding, or both. B. Single primer PCR primer disclosed herein. C diagrams dual primer PCR primers. As indicated by the same color, the 3' regions of the dual primers have sequence homology with synthesis and optionally amplification primers.

FIG. 4 presents an example of a single primer PCR amplicon in which the 5' digestible portion comprises glycosylase sensitive bases (e.g., uracil bases). Here the amplicon is digested with a glycosylase then annealed/extended with adapter primers to perform dual primer PCR. The low Tm stem structure comprising adapter primer sequence is optional. That is, the red adapter portions need not be complementary.

FIG. 5 illustrates an example of a single primer PCR amplicon in which the 5' digestible portion comprises nuclease resistant bases. Here the amplicon is digested with a 5'-3' exonuclease then annealed/extended with adapter primers to perform dual primer PCR. Stem structure comprising adapter primer sequence is optional.

FIG. 6 shows inefficient priming of an undigested single primer PCR amplicon with a dual primer PCR primer.

FIG. 7 illustrates exemplary uracil containing single and dual primer PCR amplification primers (SEQ ID NOS 2-6, respectively, in order of appearance).

FIG. 8 illustrates example exonuclease resistant single and dual primer PCR amplification primers (SEQ ID NOS 21 and 3-6, respectively, in order of appearance).

FIG. 9 presents a Bioanalyzer trace of dual primer PCR after +/−treatment with UDG of single primer PCR amplicons comprising uracil bases near the 5' end indicates that in the absence of digestion of the 5' end of a single primer PCR amplicon, annealing (and PCR) is very inefficient (SEQ ID NOS 2 and 2-4, respectively, in order of appearance).

FIG. 10 diagrams dual primer selection. Amplification with a pair of forward and reverse PCR primers, as opposed to a single forward or reverse primer, is more efficient.

FIG. 11 shows a Bioanalyzer trace of dual primer PCR after UDG digest of single primer PCR amplicons, in which PCR was performed in the presence of single or dual combinations of primers as indicated. Also shown is the threshold cycle (Ct) of the various combinations.

FIG. 12 presents a Bioanalyzer trace of dual primer PCR after UDG digest of single primer PCR amplicons, in which PCR was performed in the presence of short or long dual primer PCR primers (SEQ ID NOS 3-6, respectively, in order of appearance).

FIG. 13 shows whole genome amplification from a single cell using the single to dual primer switching method disclosed herein.

FIG. 14 illustrates typical DNA amplification workflow.

FIG. 15 illustrates typical RNA amplification workflow.

FIG. 16 illustrates typical directional RNA amplification workflow.

FIG. 17 shows exemplary primer designs used for Y adapter systems. Synthesis of primer segments as described in FIG. 3.

FIG. 18 shows exemplary primer designs used for paired adapter systems. Synthesis of primer segments as described in FIG. 3.

FIG. 19 shows priming and strand displacing primer extension on single stranded nucleic acids.

FIG. 20 shows priming and primer extension on primer extended products from FIG. 19.

FIG. 21 shows directional first strand priming and primer extension on single stranded nucleic acids.

FIG. 22 shows directional strand priming and primer extension on primer extension products from FIG. 21.

FIG. 23 shows single and dual primer amplification primers on primer extended and amplified templates.

DETAILED DESCRIPTION

The present disclosure provides methods for primer switching. More specifically, provided herein are methods for converting single primer PCR amplicons to dual primer PCR amplicons. By definition, single primer PCR produces amplicons that are 5'-3' complementary (see FIG. 1). Denaturation and cooling of such amplicons produces a mixture of intermolecular and intramolecular 5'-3' hybrids whose 3'-5' melting temperature ($T_m$) is dictated by the primer sequence. Converting these single primer amplicons to dual primer amplicons in which a 3' portion of the dual primers is complementary to a 3' portion of the single primer PCR amplicons requires annealing of the dual primers to single-stranded (i.e., denatured) single primer amplicons. However, the $T_m$ of the dual primers will necessarily be less than that of the single primer. As such, single primer PCR amplicon inter/intramolecular hybrids will anneal at a higher temperature than required for dual primer hybridization, thus inhibiting or unfavorably competing with annealing and primer extension of the dual primers. The method disclosed herein, solves this problem by using primers for the single primer PCR that allow digestion of the 5' end of the amplicon. Thus, interactions between the 5' digested ends and the 3' complementary ends are less stable, thereby allowing for annealing to a different primer.

Also provided herein are modifications of the single to dual primer switching. For example, a similar method can be used to switch between different single PCR primers. As another example, a similar method can be used to affix adapter sequences to PCR amplicons.

(I) Single Primer to Dual Primer Amplicon Switching

One aspect of the present disclosure encompasses methods for converting single primer PCR amplicons to dual primer PCR amplicons. The methods comprise: forming single primer PCR templates by contacting target nucleic acids with a plurality of synthesis primers comprising an optionally digestible 5' end and wholly or partially degenerate 3' end separated by a series of bases homologous with a dual primer PCR primer sequence and optionally any tag sequences, contacting the single primer PCR template with a primer comprising a digestible 5' portion and optionally a non-digestible 3' portion under conditions supporting amplification (Steps I, II, and III described in below); treating the single primer PCR amplicons with an enzyme capable of digesting a 5' portion of the single primer PCR amplicons to form digested amplicons (Step IV described in detail below); and amplifying the digested amplicons with a pair of PCR primers having homology to an undigested portion of the digested amplicons (Step V described in detail below), thereby forming the dual primer PCR amplicons.

Step I: Forming Single Primer PCR Amplicons

The first step of the method comprises forming single primer PCR amplicons by contacting target nucleic acids with a synthesis primer under primer extension conditions.

(a) Synthesis and Single Primer PCR Primers

Synthesis primers used herein comprise at least three portions: a 5' portion homologous with the single primer PCR primer, a nested portion optionally homologous to the 3' end of a dual primer PCR primer and 3' template targeting sequence. The 5' portion is optionally digestible. The 3' portion can be completely random, quasi random or the sum of pooled targeting primer sequences. In some embodiments the synthesis primers may include a tag sequence (also referred to herein as a barcode or index sequence) useful for monitoring synthetic direction and/or molecular identity. The single primer PCR primers comprise at least the first 5' portion of the synthesis primers and are digestible. In some embodiments the single primer PCR primers comprise two distinct portions, a digestible 5' portion and a non-digestible 3' portion (see FIG. 3B). In some embodiments, the digestible 5' portion of the single primer PCR primer comprises at least one glycosylase sensitive base. In other embodiments, the single primer PCR primer comprises at least one nuclease resistant nucleotide at an interface between the digestible 5' portion and the non-digestible 3' portion of the single primer PCR primer. The sequence of the non-digestible portion is optionally homologous to the 3' portions of the dual primer PCR primers detailed below.

In some embodiments the synthesis primers may be used in amplification conditions.

In certain embodiments, the 5' portion of the single primer PCR primer comprises one or more glycosylase sensitive bases (see FIG. 3B). Non-limiting examples of suitable glycosylase sensitive bases include uracil, 5-carboxylcytosine (5-caC), 2,6-diamino-4-hydroxy-5-formamidopyrimidine (FapyG), 4,6-diamino-5-formamidopyrimidine (FapyA), 5-formylcytosine (fC), 5-formyluracil (fU), 5-hydroxycytosine (hoC), 5-hydroxyuracil (hoU), 6-hydroxy uracil, 5,6-dihydroxy uracil, 5-hydroxymethyl cytosine (hmC), 5-hydroxymethyl uracil (hmU), hypoxanthine, 3-methyladenine(3-mA), 3-methylcytosine(3-mC), 5-methylcytosine (5-mC), 8-oxoadenine (8-oxoA), 8-oxoguanine (8-oxoG), thymine glycol (Tg), urea, or xanthine. In specific embodiments, the glycosylase sensitive base is uracil.

In general, at least 40% of the bases present in the digestible 5' portion of the single primer PCR primer are glycosylase sensitive bases. In some embodiments, at least 45%, at least 50%, at least 55%, at least 60%, at least 65% at least 70%, at least 75%, at least 80%, at least 85%, at least 90%, at least 95%, at least 99%, or at least about 100% of the bases present in the digestible 5' portion of the single primer PCR primer are glycosylase sensitive bases. In alternate embodiments, the single primer PCR primer can contain at least one, at least two, at least three, at least four, at least five, at least six, at least seven, at least eight, at least nine, at least ten, at least 11, at least 12, at least 13, at least 14, or at least 15 glycosylase sensitive bases.

In other embodiments, the single primer PCR primer comprises at least one nuclease resistant nucleotide within the 3' portion of the PCR primer or at an interface between the digestible 5' portion and the 3' portion of the PCR primer (see FIG. 3B). For example, the single primer PCR primer can comprise at least one nuclease resistant nucleotide within about 5 nucleotides to about 15 nucleotides from its 5' end. Examples of suitable nuclease resistant nucleotides include, without limit, those comprising a 3'-5' phosphorothioate linkage, a 3'-5' phosphoroborane linkage, a 2'-5' phosphodiester linkage, a 2' O-methyl moiety, a 2' fluoro moiety, a propyne base analog, or combinations thereof. For example, a nuclease resistant nucleotide can comprise a 3'-5' phosphorothioate linkage, a 3'-5' phosphoroborane linkage, or a 2'-5' phosphodiester linkage nuclease as well as a 2' fluoro moiety, and/or a propyne base analog. In some embodiments, the non-digestible 3' portion or the interface between the digestible 5' portion and the non-digestible 3' portion of the single primer PCR primer comprises at least two, at least three, at least four, at least five, at least 6, at least 7, at least 8, at least none, at least ten, at least eleven, or at least twelve nuclease resistance nucleotides.

The length of the single primer PCR primer can vary. In general, the single primer PCR primer can range in length from about 14 nucleotides to about 40 nucleotides. In various embodiments, the single primer PCR primer can be about 14, 15, 16, 17, 18, 18, 20, 21, 22, 23, 24, 25, 26, 27, 28, 29, 30, 31, 32, 33, 34, 35, 36, 37, 38, 39, or 40 nucleotides in length. In some embodiments, the digestible 5' portion can be about 5, 6, 7, 8, 9, 10, 11, 12, 13, 14, 15, 16, 17, 18, 19, or 20 nucleotides in length, and the non-digestible 3' portion can be about 5, 6, 7, 8, 9, 10, 11, 12, 13, 14, 15, 16, 17, 18, 19, or 20 nucleotides in length. In specific embodiments, the digestible 5' portion can range in length from about 8 to about 14 nucleotides, and the non-digestible 3' portion can range in length from about 10 to about 16 nucleotides.

In some embodiments, the synthesis primer can further comprise a degenerate region at the 3' end. A degenerate nucleotide can have 2-fold degeneracy (i.e., it can be one of two nucleotides), 3-fold degeneracy (i.e., it can be one of three nucleotides), or 4-fold degeneracy (i.e., it can be one of four nucleotides, A or C or G or T). Nucleotides having 3-fold degeneracy include "B" (can be C or G or T), "D" (can be A or G or T), "H" (can be A or C or T), and "V" (can be A or C or G). Nucleotides having 2-fold degeneracy include "K" (can be G or T), "M" (can be A or C), "R" (can be A or G), "Y" (can be C or T), "S" (can be C or G), and "W" (can be A or T). The degenerate region can range in length from about 4 to about 18 nucleotides. In certain embodiments, degenerate region can be about 4, 5, 6, 7, 8, 9, 10, 11, 12, 13, 14, 15, 16, 17, or 18 nucleotides in length. Such degeneracy can arise from mixed base synthetic methods or pooling individually synthesized oligonucleotides.

In general, the synthesis primers and single primer PCR primers are single-stranded and have a hydroxyl group at the 3' end for priming DNA synthesis. The amplification primers can comprise deoxyribonucleotides, ribonucleotides, or combinations thereof. The nucleotides can be standard nucleotides (i.e., adenosine, guanosine, cytidine, thymidine/uridine) or nucleotide analogs. A nucleotide analog refers to a nucleotide having a modified purine or pyrimidine base and/or a modified ribose moiety. A nucleotide analog can be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The design of synthesis and amplification primers will depend on intended use and adapter primer design.

In general, the single primer PCR primer will have an average GC content of about 40-60%, and an average melting temperature ($T_m$) of about 50° C. to about 85° C. In certain embodiments, the single primer PCR primer can have a $T_m$ of about 50° C., about 55° C., about 60° C., about 65° C., about 70° C., about 75° C., about 80° C., or about 75° C.

The synthesis and amplification primer design depends on the downstream adapter system. In all cases the synthesis primer will comprise a digestible segment homologous with all or part of the amplification primer, nested non-digestible segment homologous with all or part of the adapter primer sequence, an optional tag sequence(s) used for directional and or molecule barcoding and a 3' template priming section (see FIGS. 3A and 3B). The template priming segment may be completely degenerate (all N's) or a pool of specific priming sequences and any composition in between. For Y adapter applications there may be one digestible+one nested non-digestible segment (see FIG. 17). The nested non digestible segment would be homologous with the sequence of the Y adapter stem. For paired adapter applications there will be two synthesis primers: one digestible amplification+two nested adapter primer segments. Amplification primers will comprise digestible and non-digestible segments for Y adapter applications while only digestible segments for paired adapter applications (see FIG. 18).

The single primer PCR primer can be designed using readily available primer design software (e.g., Primer3, PrimerQuest Tool, NPprimer, Multiplex primer design, etc.), and can be synthesized using standard oligonucleotide chemical synthesis methods.

(b) Oligonucleotides

One aspect of the disclosure encompasses an artificial oligonucleotide comprising a random, semi-random or pool of specific 3' sequences, a fixed 5' sequence, an optional internal tag sequence, and a nested sequence between the 5' sequence and the internal tag and/or 3' template targeting sequence (see FIG. 3A). A further aspect provides a plurality of artificial oligonucleotides comprising a plurality of first oligonucleotides and a plurality of second oligonucleotides that may be used for directional amplification of RNA. Each oligonucleotide of the plurality of first oligonucleotides comprises a random, semi-random or pool of specific 3' sequences, a fixed 5' sequence optionally comprising at least one digestible residue, a nested sequence homologous to an adapter sequence, and optionally an internal tag sequence comprising a first tag sequence. Each oligonucleotide of the plurality of second oligonucleotides comprises a random, semi-random or pool of specific 3' sequence, a fixed 5' sequence comprising at least one deoxyuridine residue, a nested sequence corresponding to an adapter sequence, and optionally an internal tag sequence comprising a second tag sequence, provided that either one or both of the pluralities of first and second oligonucleotides comprises the first and/or second tag sequence (see FIGS. 21 and 22).

In general, the oligonucleotides are single-stranded. The nucleotides can be deoxyribonucleotides or ribonucleotides. The oligonucleotides can comprise standard nucleotides (i.e., A, C, G, T, U, dU, and so forth), as well as nucleotide analogs. A nucleotide analog refers to a nucleotide having a modified purine or pyrimidine base and/or a modified ribose moiety. A nucleotide analog can be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos. The backbone of the oligonucleotides can comprise phosphodiester linkages, as well as phosphothioate, phosphoramidite, or phosphorodiamidate linkages.

(i) 3' Sequence

Each oligonucleotide in the plurality of oligonucleotides comprises a random, semi-random or pool of specific 3' sequences (see FIG. 3A). The random or semi-random sequence generally has sufficient complementarity to target nucleic acids such that the 3' sequence of the oligonucleotide hybridizes with the target RNA (or cDNA product). In some embodiments, the 3' sequence can be random and consist of 4-fold degenerate nucleotides (i.e., N). For example, the 3' sequence can be poly-N. In other embodiments, the 3' sequence can be semi-random and comprise at least one 2-fold, 3-fold, or 4-fold degenerate nucleotide. In certain embodiments, the 3' sequence can comprise 2-fold degenerate nucleotides (i.e., K, M, R, Y, and/or S), 3-fold degenerate nucleotides (i.e., B, D, H, and/or V), 4-fold degenerate nucleotides, or combinations thereof. In specific embodiments, the 3' sequence can comprise a combination of N and K (i.e., G and T) degenerate nucleotides. For example, the 3' sequence can comprise about equal numbers of N and K nucleotides that are arranged in any order. Examples of suitable "NK" sequences include 5'-KNNNKNKNK-3', 5'-NNNKNKKNK-3', and 5'-NKNNKNNKK-3'. In additional embodiments, the 3' sequence can comprise a combination of non-degenerate and degenerate nucleotides. For example, the 3' sequence can comprise a poly-dT sequence and degenerate nucleotides at the 3' end. Examples of such sequences include poly-dT-NN, poly-dT-VN, and the like. In still further embodiments, the 3' sequence can comprise a combination of any of the foregoing sequences. As an example, the combination of 5'-KNNNKNKNK-3', 5'-NNNKNKKNK-3', 5'-NKNNKNNKK-3', and poly-dT14-VN (SEQ ID NO: 20) are available in the Complete Whole Transcriptome Amplification Kit (WTA2); Sigma-Aldrich.

The length of the 3' sequence can and will vary. In general, the 3' sequence can range from about 5 nucleotides to about 30 nucleotides in length. In certain embodiments, the 3' sequence can be about 5, 6, 7, 8, 9, 10, 11, 12, 13, 14, 15, 16, 17, 18, 19, 20, 21, 22, 23, 24, 25, 26, 27, 28, 29, or 30 nucleotides in length. In specific embodiments, the 3' sequence can range from about 6 to about 20 nucleotides in length.

(ii) 5' Sequence

Each oligonucleotide comprises a fixed 5' sequence (see FIGS. 3A and 3B). In some embodiments the 5' sequence comprises non-complementary nucleotides, thereby reducing intramolecular interactions within each oligonucleotide and/or intermolecular interactions between the 5' sequences of oligonucleotides in a plurality of oligonucleotides. Examples of non-complementary nucleotides include K (i.e., G and T), M (i.e., A and C), R (i.e., A and G), or Y (i.e., C and T). Moreover, the non-complementary nucleotides are chosen such that at least one thymidine residue can be replaced with a deoxyuridine residue. Thus, the 5' sequence can comprise K (i.e., G and T) or Y (i.e., C and T) nucleotides, in which one or more thymidine residues are replaced with deoxyuridine (dU). In specific embodiments, the 5' sequence can comprises G and dU residues. In some embodiments, the 5' sequence can contain one, two, three, four, five, six, seven, eight, or more dU residues.

The length of the fixed 5' sequence can and will vary. In general, the fixed 5' sequence can range from about 5 nucleotides to about 40 nucleotides in length. In certain embodiments, the fixed 5' sequence can be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length. In specific embodiments, the fixed 5' sequence can range from about 6 to about 18 nucleotides in length.

(iii) Nested Sequence

Each oligonucleotide further comprises a nested sequence at the 3' end of the fixed 5' sequence (see FIG. 3A). The nested sequence has homology to a region of an adapter sequence. For example, the nested sequence can have homology to the double-stranded region of an adapter sequence (e.g., from Illumina® (San Diego, Calif.)). The nested sequence can have homology to a region of other adapters, which are known in the art.

The length of the nested sequence can and will vary. In general, the nested sequence can range from about 5 nucleotides to about 25 nucleotides in length. In certain embodiments, the 5' sequence can be about 5, 6, 7, 8, 9, 10, 11, 12, 13, 14, 15, 16, 17, 18, 19, 20, 21, 22, 23, 24, or 25 nucleotides in length. In specific embodiments, the nested sequence can range from about 8 to about 15 nucleotides in length.

(iv) Internal Tag Sequence

Each oligonucleotide also can comprise an optional internal tag (or barcode) sequence (see FIG. 3A). In general, the tag sequence lies between the nested sequence (at the 3' end of the fixed 5' sequence) and the random, semi-random or pool of specific 3' sequences. Tag sequences serve to tag cDNA products with respect to the orientation of the starting RNA molecule and/or molecular identity. If the oligonucleotide contains the optional tag sequence, the tag sequence can be a first tag sequence, which functions to mark the orientation of the 3' end of the RNA, or a second tag sequence, which functions to mark the orientation of the 5' end of the RNA.

The nucleotide sequences of the tag sequences can and will vary. In general, the tag sequences are artificial sequences that are not present in the target RNA molecule(s). The content of nucleotides in the artificial tag sequence can be balanced to provide a diversity of G/T and C/A. Additionally, the first and second oligonucleotides can be balanced per Watson-Crick base pairing to address bias occurring during primer annealing to the target nucleic acid.

In general, the tag sequences can range in length from about 4 nucleotides to about 20 nucleotides. In various embodiments, the tag sequence can range from about 5 nucleotides to about 15 nucleotides in length, from about are 6 nucleotides to about 12 nucleotides in length, or from about 7 nucleotides to about 10 nucleotides in length. In some embodiments, the tag sequence is at least 6 nucleotides in length. In other embodiments, the tag sequence is 7 nucleotides in length, 8 nucleotides in length, or 9 nucleotides in length.

(c) Target Nucleic Acids

The method comprises forming single primer PCR amplicons by contacting target nucleic acids with a synthesis primer under primer extension conditions followed by contacting with a single primer PCR primer under amplification conditions. A variety of target nucleic acids can be amplified by single primer PCR. In some embodiments, the target nucleic acids can be genomic DNA. The genomic DNA can be nuclear, mitochondrial, or plastid. In some embodiments, the target nucleic acids can comprise a genomic library, i.e., the whole genome of a cell or a population of cells. In other embodiments, the target nucleic acids can be complementary DNA (cDNA) transcribed from messenger RNA (mRNA) or non-coding RNA (e.g., micro RNA (miRNA), long noncoding RNA (lncRNA), long intergenic non-coding RNA (lincRNA), small interfering RNA (siRNA), Piwi-interacting RNA (piRNA), trans-acting RNA (rasiRNA), ribosomal RNA (rRNA), transfer RNA (tRNA), mitochondrial tRNA (MT-tRNA), small nuclear RNA (snRNA), small nucleolar RNA (snoRNA), SmY RNA, Y RNA, spliced leader RNA (SL RNA), and/or telomerase RNA component). In certain embodiments, the target nucleic acid can be a library of cDNAs derived from the transcriptome of a cell or population of cells. Persons skilled in the art are familiar with means (e.g., standard protocols, commercially available kits, etc.) for isolating genomic DNA, isolating RNA, and/or preparing cDNA from RNA.

The target nucleic acids can be wild-type, can contain single nucleotide polymorphisms (SNPs), can contain multiple nucleotide substitutions, can contain insertions and/or deletions (indels), and/or can contain epigenetic modifications (e.g., methylated cytosines, other modified nucleotides, and the like).

The target nucleic acids can be derived from eukaryotic, archaeal, or bacterial cells. Suitable eukaryotic cells include mammalian cells (e.g., human, primates, dogs, cats, farm animals, zoo animals, rodents, research animals, etc.), non-mammalian vertebrate cells (e.g., poultry, fish, frog, and the like), plant cells (e.g., maize, legumes, grasses, brassicas, and so forth), invertebrate cells (e.g., insects, worms, etc.), fungal cells, single-celled organisms, and the like.

Amount of target nucleic acid included in the amplification reaction can range from about 1 attogram (ag) to about 100 nanograms (ng). In some embodiments, a single (mammalian) cell provides the target nucleic acids.

(d) Amplification Conditions

The synthesis primer then single primer PCR primer, as detailed above, is contacted with the target nucleic acid, as detailed above, under amplification conditions to form the single primer PCR amplicons. The amplification conditions comprise amplification via polymerase chain reaction (PCR) (see FIGS. 14, 15, and 16).

PCR comprises contact with a DNA polymerase and deoxyribonucleotides (e.g., dNTPs) in the presence of a suitable buffer. In general, the DNA polymerase used for PCR amplification has polymerase activity and optionally 3' to 5' proofreading exonuclease activity. In general, the DNA polymerase will be thermophilic (e.g., Taq DNA polymerase, Pfu DNA polymerase, Tli DNA polymerase, Tfl DNA polymerase, Tth DNA polymerase, Bst DNA polymerase, Pwo DNA polymerase, KOD DNA polymerase, variants thereof, or combinations thereof). Alternatively, the DNA polymerase can be mesophilic (e.g., E. coli DNA polymerase I, Klenow fragment of E. coli DNA polymerase I, phi29 DNA polymerase, T7 DNA polymerase, T4 DNA polymerase, variants thereof, or combinations thereof).

The PCR amplification reaction can be routine PCR, real time PCR, quantitative PCR, fast PCR, Hot Start PCR, touchdown PCR, multiplex PCR, long range PCR, and the like. Alternatively the amplification reaction can be multiple displacement amplification (MDA), transcription mediated amplification (TMA), nucleic acid sequence-based amplification (NASBA), strand displacement amplification (SDA), loop-mediated isothermal amplification (LAMP), helicase-dependent amplification (HAD), nicking enzyme amplification reaction (NEAR), rolling circle amplification (RCA), or ligation mediated amplification.

The PCR amplification reaction comprises cycling between denaturation steps and annealing/extending steps. The total number of cycles can range from about 10 to about 60. The annealing/extending can occur during a single step, or annealing/extending can occur during separate annealing and extending steps. In general, the temperature of the denaturation step can range from about 90° C. to about 100° C., and the duration of the denaturation step can range from about 10 seconds to about 10 minutes. A single annealing/extending step can range from about from about 50° C. to about 75° C., and the duration of the single annealing/extending step can range from about 1 minute to about 12 minutes. Alternatively, the temperature of an annealing step can range from about 50° C. to about 75° C., and the duration of the annealing step can range from about 20 seconds to about 12 minutes, and the temperature of the extension step can range from about 68° C. to about 75° C., and the duration of the extension step can vary from about 20 seconds to about 5 minutes. The final extension step can be followed by a terminal elongation step at the extension temperature that lasts for about 5 minutes, 10 minutes, or longer.

The first step of the method disclosed herein, therefore, generates single primer PCR amplicons that comprise a digestible 5' portion. In some embodiments, the single primer PCR amplicons comprise one or more glycosylase sensitive base near the 5 end of the amplicon. In other embodiments, the single primer PCR amplicons comprise one or more nuclease resistant nucleotides near the 5' end of the amplicon. Upon denaturation of the double-stranded amplicons, the single-stranded amplicons can form intramolecular (hairpin) and/or intermolecular structures because the 5' and 3' ends of amplicons produced during single primer PCR reaction are complementary (see FIGS. 1, 2, 4, and 5).

Step II: Non-Directional or Directional Amplification of DNA or RNA

In Step II, DNA or RNA is amplified non-directionally or directionally as described below in sections Step II$^{Non\text{-}Directional}$ and Step II$^{Directional}$, respectively.

Step II$^{Non\text{-}Directional}$: Non-Directional Amplification of DNA or RNA

For DNA, the non-directional amplification step comprises replicating at least one DNA molecule in the presence of a plurality of synthesis primers to generate a plurality of double stranded templates, wherein each of the plurality of synthesis primers comprises (5' to 3') a fixed optionally digestible 5' sequence, a nested sequence having complementarity to an adapter sequence, an optional tag sequence, and a random, semi-random or pool of specific 3' sequence having complementarity to the DNA molecules of interest (see FIG. 14).

For RNA, the non-directional process comprises reverse transcribing at least one RNA molecule in the presence of a plurality of synthesis primers to generate a plurality of double stranded cDNA templates, wherein each of the plurality of synthesis primers comprises (5' to 3') a fixed optionally digestible 5' sequence, a nested sequence having complementary to an adapter sequence, an optional tag sequence, and a random, semi-random or pool of specific 3' sequences having complementarity to the DNA molecules of interest (see FIG. 15).

Non-Directional Sub-Step A—Library Synthesis

The lone step of the non-directional amplification process comprises replicating at least one DNA or reverse transcribing at least one RNA molecule in the presence of a plurality of first synthesis primers to generate a plurality of double stranded templates (see FIGS. 14, 15, 19, and 20).

(i) Nucleic Acids

A variety of different types of RNA molecules can be amplified using the processes disclosed herein. In some embodiments, the RNA can be a messenger RNA (mRNA) or a fragment thereof. The mRNA can be polyadenylated or the mRNA can be non-polyadenylated. In certain embodiments, the RNA can be a population of different mRNAs. In other embodiments, the RNA can be a non-coding RNA (ncRNA). For example, the ncRNA can be long noncoding RNA (lncRNA), long intergenic non-coding RNA (lincRNA), micro RNA (miRNA), small interfering RNA (siRNA), Piwi-interacting RNA (piRNA), trans-acting RNA (rasiRNA), ribosomal RNA (rRNA), transfer RNA (tRNA), mitochondrial tRNA (MT-tRNA), small nuclear RNA (snRNA), small nucleolar RNA (snoRNA), SmY RNA, Y RNA, spliced leader RNA (SL RNA), telomerase RNA component (TERC), fragments thereof, or combinations thereof. In still further embodiments, the RNA can be the transcriptome of a cell or population of cells. The RNA can be derived from eukaryotic, archaeal, or bacterial cells.

A variety of types of DNA molecules can be amplified. This may include, for example, eukaryotic, prokaryotic, archaeal, plasmids, phage, synthetic, etc.

The amount of input nucleic acid can and will vary. In general, the processes disclosed herein can amplify low or single cell input quantities of nucleic acids. In some embodiments, the amount of input nucleic acid can be at least about 10 femtograms (fg), 100 fg, 5 picograms (pg), at least about 10 pg, at least about 20 pg, at least about 50 pg, at least about 100 pg, at least about 200 pg, at least about 500 pg, or more than about 500 pg of nucleic acid. In specific embodiments, the amount of input nucleic acid can range from about 10 pg to about 100 pg.

The quality or integrity of nucleic acid also can vary. For example, the quality of input RNA can range from low quality (i.e., degraded or fragmented) to high quality (i.e., intact). Persons skilled in the art are familiar with means to estimate the quality of the RNA of interest. For example, the quality of total RNA can be estimated on the basis of the ratio of 28S rRNA to 18S rRNA. In some embodiments, the RNA can have a 28S:18S ratio of at least about 2:1, a 28S:18S ratio of at least about 1:1, a 28S:18S ratio of less than about 1:1, or an undetectable 28S:18S ratio.

(ii) Double Stranded Template Synthesis

The RNA molecule or molecules are contacted with a plurality of synthesis primers (see FIGS. 3A and 19). The synthesis primers are detailed above. Each synthesis primer comprises (5' to 3') a fixed 5' sequence optionally digestible, a nested sequence having homology to an adapter sequence, an optional internal tag sequence, and a random, semi-random or pool of 3' sequences having complementarity to the RNA molecule.

Upon contact with the target nucleic acid, the 3' sequences of the synthesis primers hybridize with complementary regions of the nucleic acid. For RNA, synthesis of the first strands of cDNA is catalyzed by a strand displacing reverse transcriptase (RT) in the presence of deoxyribonucleotides (i.e., dCTP, dGTP, dATP, and dTTP) and a suitable RT buffer. Second strand synthesis is catalyzed by a strand displacing DNA polymerase The polymerase activities may be from single or multiple enzymes. For DNA synthesis of the first and second strands of DNA is catalyzed by a strand displacing DNA polymerase in the presence of deoxyribonucleotides (i.e., dCTP, dGTP, dATP, and dTTP) and a suitable buffer. Those skilled in the art are familiar with appropriate concentrations of the reactants and suitable reaction conditions for reverse transcriptional dnDNA replication.

The reverse transcriptase can be mesophilic or thermophilic, and the reverse transcriptase can be RNAaseH$^+$ or RNAaseH$^-$. Examples of suitable reverse transcriptases include M-MLV RT (from Moloney murine leukemia virus), HIV-1 RT (from human immunodeficiency virus type 1), AMV RT (from avian myeloblastosis virus), variants thereof, and engineered versions thereof. DNA polymerase may be mesophilic or thermophilic. Examples include pol I, Klenow polymeases, Klenow exo minus polymerase, T4 DNA polymerase, Bst polymerase, Taq polymerase, phi29 polymerase, T7 polymerase, and the like.

Upon completion of the double stranded template, the reverse transcriptase and/or DNA polymerase can be inactivated by heat treatment. The heat inactivation can be at a temperature of about 70° C., about 80° C., or about 90° C. for about 3 minutes, about 5 minutes, about 10 minutes, or about 15 minutes. In general, the lower the inactivation temperature the longer the duration of the heating step.

Step II$^{Directional}$: Directional Amplification of RNA

Alternatively, Step II may involve directionally amplifying RNA and preparing the amplified product for sequencing. The directional amplification process comprises two sub-steps A and B described below.

In general, sub-step A comprises reverse transcribing at least one RNA molecule in the presence of a plurality of first synthesis primers to generate a plurality of first strands of cDNA (see FIG. 21), wherein each of the plurality of first synthesis primers comprises (5' to 3') a fixed optionally digestible 5' sequence, a nested sequence having complementarity to an adapter sequence, an optional internal tag sequence comprising a first tag sequence, and a random, semi-random or pool of specific 3' sequence having complementarity to the RNA molecules of interest. Preferably in sub-step A, the reverse transcribing is performed in the presence of actinomycin D, as this tends to mitigate antisense artifacts from re-copying of the cDNA by retroviral reverse transcriptase. See Ruprecht et al., Biochim Biophys Acta. 1973 Jan. 19; 294(2):192-203; Perocchi et al., Nucleic Acids Res. 2007; 35(19):e128. Sub-step B (see FIG. 22) comprises replicating the plurality of first strands of cDNA in the presence of a plurality of second synthesis primers and, preferably, a non-strand displacing DNA polymerase to generate a plurality of double-stranded cDNA products, wherein each of the plurality of second synthesis primers comprises (5' to 3') a fixed 5' sequence optionally digestible, a nested sequence having complementary to an adapter sequence, an optional internal tag sequence comprising a second tag sequence, and a random, semi-random or pool of 3' sequences having complementarity to a first strand of cDNA.

Directional Sub-Step A—First Strand cDNA Synthesis

Sub-step A of the directional amplification step comprises reverse transcribing at least one RNA molecule in the presence of a plurality of first synthesis primers to generate a plurality of first strands of cDNA (see FIG. 21).

(i) RNA

A variety of different types of RNA molecules can be amplified using the processes disclosed herein. In some embodiments, the RNA can be a messenger RNA (mRNA) or a fragment thereof. The mRNA can be polyadenylated or the mRNA can be non-polyadenylated. In certain embodiments, the RNA can be a population of different mRNAs. In other embodiments, the RNA can be a non-coding RNA (ncRNA). For example, the ncRNA can be long noncoding RNA (lncRNA), long intergenic non-coding RNA (lincRNA), micro RNA (miRNA), small interfering RNA (siRNA), Piwi-interacting RNA (piRNA), trans-acting RNA (rasiRNA), ribosomal RNA (rRNA), transfer RNA (tRNA), mitochondrial tRNA (MT-tRNA), small nuclear RNA (snRNA), small nucleolar RNA (snoRNA), SmY RNA, Y RNA, spliced leader RNA (SL RNA), telomerase RNA component (TERC), fragments thereof, or combinations thereof. In still further embodiments, the RNA can be the transcriptome of a cell or population of cells. The RNA can be derived from eukaryotic, archaeal, or bacterial cells.

The amount of input RNA can and will vary. In general, the processes disclosed herein can amplify low or single cell input quantities of RNA. In some embodiments, the amount of input RNA can be at least about 5 picograms (pg), at least about 10 pg, at least about 20 pg, at least about 50 pg, at least about 100 pg, at least about 200 pg, at least about 500 pg, or more than about 500 pg of RNA. In specific embodiments, the amount of input RNA can range from about 10 pg to about 100 pg.

The quality or integrity of RNA also can vary. For example, the quality of input RNA can range from low quality (i.e., degraded or fragmented) to high quality (i.e., intact). Persons skilled in the art are familiar with means to estimate the quality of the RNA of interest. For example, the quality of total RNA can be estimated on the basis of the ratio of 28S rRNA to 18S rRNA. In some embodiments, the RNA can have a 28S:18S ratio of at least about 2:1, a 28S:18S ratio of at least about 1:1, a 28S:18S ratio of less than about 1:1, or an undetectable 28S:18S ratio.

(ii) First Strand Synthesis

The RNA molecule or molecules are contacted with a plurality of first synthesis primers (see FIG. 21). The first synthesis primers are detailed above. Each first synthesis primer comprises (5' to 3') a fixed 5' sequence optionally digestible, a nested sequence having homology to an adapter sequence, an optional internal tag sequence comprising a first tag sequence, and a random, semi-random or pool of 3' sequences having complementarity to the RNA molecule.

Upon contact with the target RNA, the 3' sequences of the first synthesis primers hybridize with complementary regions of the RNA. Synthesis of the first strands of cDNA is catalyzed by a reverse transcriptase (RT) in the presence of deoxyribonucleotides (i.e., dCTP, dGTP, dATP, and dTTP) and a suitable RT buffer (see FIG. 21). Those skilled in the art are familiar with appropriate concentrations of the reactants and suitable reaction conditions for first strand cDNA synthesis.

The reverse transcriptase can be mesophilic or thermophilic, and the reverse transcriptase can be RNAaseH$^+$ or RNAaseH$^-$. Examples of suitable reverse transcriptases include M-MLV RT (from Moloney murine leukemia virus), HIV-1 RT (from human immunodeficiency virus type 1), AMV RT (from avian myeloblastosis virus), variants thereof, and engineered versions thereof.

As noted above, in some embodiments, first strand cDNA synthesis can be conducted in the presence of actinomycin D to reduce undesired priming from strand-displaced, first strands of cDNA. However, some stand displacement and second strand extension may occur, generating background product flanked with downstream barcode. The use of actinomycin D can reduce the level of products flanked with the same barcode sequences.

Upon completion of the first strand synthesis reaction, the reverse transcriptase can be inactivated by heat treatment. The heat inactivation can be at a temperature of about 70° C., about 80° C., or about 90° C. for about 3 minutes, about 5 minutes, about 10 minutes, or about 15 minutes. In general, the lower the inactivation temperature the longer the duration of the heating step.

(iii) Removal of Single-Stranded First Synthesis Primers

The process further comprises contacting the plurality of first strands of cDNA with a single strand specific 3'-5' deoxyribonuclease (i.e., exonuclease) to degrade single-stranded (i.e., unhybridized) first synthesis primers. Double-stranded cDNA-RNA hybrids are not degraded by contact with preferred 3'-5' deoxyribonucleases. In some embodiments, the 3'-5' deoxyribonuclease can be E. coli exonuclease I, E. coli exonuclease X, or mammalian Trex1 (DNase III). In specific embodiments, the 3'-5' deoxyribonuclease can be E. coli exonuclease I. The amount of exonuclease used to degrade the excess first synthesis primers can and will vary depending upon a variety of factors including the starting quantity of first synthesis primers used in sub-step A. In general, contact with the exonuclease is performed at a temperature ranging from about 35° C. to about 40° C. for a period of time from about 5 minutes to about 60 minutes. The exonuclease can be inactivated with heat described herein (e.g., at a temperature of about 70° C., about 80° C., or about 90° C. for about 3 minutes, about 5 minutes, about 10 minutes, or about 15 minutes).

Directional Sub-Step B—Second Strand cDNA Synthesis

Sub-step B of the directional amplification step comprises replicating the plurality of first strands of cDNA in the presence of a plurality of second synthesis primers to generate a plurality of double-stranded cDNA products (see FIG. 22).

(i) Second Strand Synthesis

Each second synthesis primer comprises (5' to 3') a fixed 5' sequence optionally comprising digestible residues, a nested sequence having complementary to an adapter sequence, an optional internal tag sequence comprising a second tag sequence, and a random, semi-random or pool of specific targeting 3' sequence having complementarity to a first strand of cDNA. The first and second synthesis primers are chosen such that either one or both comprise the first and/or second tag sequence.

This step of the process commences with heat denaturing the cDNA/RNA duplexes generated during step A in the presence of the plurality of second synthesis primers. The heat treatment generates single-stranded cDNA templates and also inactivates the 3'-5'-exonuclease used to degrade the single-stranded first synthesis primers. The heat treatment can be at a temperature of about 90° C., about 92° C., about 94° C., about 96° C., or about 100° C. for about 1 minute, about 2 minutes, about 5 minutes, or about 10 minutes. After the heat treatment, the temperature is lowered to the reaction temperature and, as the temperature falls, the 3' sequences of the second synthesis primers hybridize with complementary regions of the first strands of cDNA (see FIG. 22).

Synthesis of the second strand of cDNA is catalyzed by a non-strand-displacing DNA polymerase in the presence of deoxyribonucleotides and a suitable buffer (see FIG. 22). The non-strand-displacing DNA polymerase can be mesophilic or thermophilic. Examples of suitable non-strand-displacing DNA polymerases include E. coli DNA polymerase I, T4 DNA polymerase, T7 DNA polymerase, variants thereof, and engineered versions thereof. Those skilled in the art are familiar with appropriate concentrations of reactants and suitable reaction conditions for second strand cDNA synthesis. Each double-stranded cDNA product is flanked by at least one of the first and second tag sequences, which indicate the orientation of the cDNA product with respect to the input RNA molecule (see FIG. 22).

Although second-strand synthesis is driven by a non-strand-displacing DNA polymerase, some background product may also be generated.

(ii) Optional Removal of Single-Stranded Second Oligonucleotides

The process optionally can further comprise contact with a 3'-5' deoxyribonuclease (i.e., exonuclease) to degrade single-stranded (i.e., unhybridized) second synthesis primers, essentially as described above for removing first strand synthesis primers.

(ii) "Single-Tube" Process

Sub-steps A and B of the directional amplification disclosed herein proceed sequentially without intervening purification steps. No purification steps allows for a single tube format, avoiding material loss. A single-tube format is also amenable to high throughput. The lack of purification steps is accomplished by step-wise exonuclease removal of the first and second oligonucleotides, and heat-inactivation of enzymes.

Step III: Amplification

Irrespective of whether DNA, non-directional or directional RNA amplification processes are employed in Step II$^{Non\text{-}Directional}$ or Step II$^{Directional}$, the next step of the methods described herein comprises amplifying the plurality of double-stranded DNA products in the presence of the one or more amplification primers to generate an amplified library of DNA products.

(i) Amplification Primers

The amplification primer comprises the fixed digestible 5' sequence and when appropriate a 3'sequence homologous to the nested portion of the synthesis primers. In general, the amplification primers are single-stranded and comprise deoxyribonucleotides. The deoxyribonucleotides can comprise the standard nucleotides (i.e., A, C, G, T, U, dU, and so forth), as well as nucleotide analogs. A nucleotide analog refers to a nucleotide having a modified purine or pyrimidine base and/or a modified ribose moiety. A nucleotide analog can be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids, peptide nucleic acids, and morpholinos. The backbone of the amplification primers can comprise phosphodiester linkages, as well as phosphothioate, phosphoramidite, or phosphorodiamidate linkages. (See FIG. 3B).

(ii) Amplification Reaction

Amplification commences with a step of heat denaturing the plurality of double-stranded DNA products generated above in the presence of the amplification primers. The heat treatment generates single-stranded templates. The heat treatment can be at a temperature of about 90° C., about 92° C., about 94° C., about 96° C., or about 100° C. for about 15 sec, 30 sec, 45 sec, 1 minute, about 2 minutes, about 5 minutes, or about 10 minutes.

After the heat treatment, the temperature is lowered to the annealing or annealing/extension temperature to permit annealing of the amplification primers to the DNA template strands. As the temperature falls, intra-molecular hybridization of 5-3' complementary sequences at the ends of short products prevents annealing of the amplification primers to these products. For directional RNA amplification, background products generated from priming strand displaced sequences will have greater 5'-3' complementarity than first and second strand primed products and thus hypothetically amplify less efficiently. By the same logic, any product having different upstream or downstream barcodes derived from strand displaced priming will amplify more efficiently.

Amplification of the DNA products is performed in the presence of a thermostable DNA polymerase, deoxyribonucleotides, and a suitable buffer. The thermostable DNA polymerase can be Taq DNA polymerase, Pfu DNA polymerase, Tli (also known as Vent) DNA polymerase, Tfl DNA polymerase, Tth DNA polymerase, variants thereof, and combinations thereof. Buffers (with or without magnesium) suitable for a thermocycling reaction are well known in the art.

In embodiments in which a single amplification primer is used, the process can comprise 3 steps (i.e., denaturation, annealing, and extension) or 2 steps (i.e., denaturation and annealing/extension). For example, in embodiments in which the melting temperature of the amplification primer is lower than 70° C., the amplification process can comprise 3 steps. Alternatively, in embodiments in which the melting temperature of the amplification primer is equal to or higher than 70° C., the amplification process can comprise 2 steps. In embodiments in which more than one amplification primer is used, the process generally comprises 3 steps (i.e., denaturation, annealing, and extension). The temperature of the annealing or annealing/extension step can and will vary, e.g., from about 50° C. to about 75° C. The temperature of the extension or annealing/extension can range from about 70° C. to about 75° C., or about 72° C. The duration of the steps of the amplification can vary from seconds to minutes. In general, the duration of the extension or annealing/extension step can range from 1 to 5 minutes. (See PCR1 steps in FIGS. 14, 15, and 16).

Step IV: Digestion

Following amplification in Step III is a digestion (see Digest steps in FIGS. 14, 15, and 16). This Step IV comprises contacting the amplified library of DNA products with a digestion enzyme. In some embodiments the digestion enzyme is uracil DNA glycosylase (UDG). Treatment with UDG hydrolyses uracil bases at the 5' ends of the amplified cDNA products, effectively weakening the terminal base pairing of each amplicon. The UDG can be of bacterial, yeast, or mammalian origin. In some embodiments, the UDG is from *E. coli*. The amount of UDG contacted with the amplified library of cDNA products can and will vary. Skilled persons can readily determine the appropriate amount and suitable reaction conditions (e.g., temperature, duration, and the like). In another embodiment for primer switching, treatment with exonuclease removes 5' bases from the amplicon until nuclease resistant bases are encountered, effectively eliminating the terminal base pairing of each amplicon. In some embodiments, the exonculease is T7 exonuclease. The amount of exonuclease contacted with the amplified library of DNA products can and will vary. Skilled persons can readily determine the appropriate amount and suitable reaction conditions (e.g., temperature, duration, and the like).

(i) Glycosylases

In embodiments in which the single primer PCR amplicons comprise one or more glycosylase sensitive bases near the 5' ends of the amplicons, the single primer PCR amplicons are contacted with at least one glycosylase. The glycosylase hydrolyzes or excises the glycosylase sensitive bases from the 5' ends of the single primer PCR amplicons, thereby weakening base pairing between the 5' and 3' ends of the amplicons (see FIG. 4).

Depending upon the identity of the glycosylase sensitive bases in the single primer PCR amplicons, the glycosylase can be a uracil DNA glycosylase, a thymine DNA glycosylase, a thymine glycol DNA glycosylase, an 8-oxoguanine DNA glycosylase, a 3-methylpurine DNA glycosylase, a Nth DNA glycosylase, a Nei DNA glycosylase, a MutY/Mig DNA glycosylase, or an alkyladenine-DNA glycosylase. For example, uracil DNA glycosylase excises uracil bases; thymine DNA glycosylase excises 5-carboxylcytosine bases; thymine glycol DNA glycosylase excises thymine glycol bases; and so forth.

The glycosylase can be of bacterial, archaeal, yeast, or mammalian origin. The glycosylase can be mesophilic or thermophilic. The amount of glycosylase contacted with the single primer PCR amplicons can and will vary depending upon, e.g., the identity of the glycosylase enzyme, the number of glycosylase sensitive bases in the amplicons, and so forth. Persons skilled in the art can readily determine the appropriate amount. The temperature of the glycosylase reacting step can range from about 20° C. to about 80° C. and the duration of the glycosylase reacting step can range from about 5 minutes to about 2 hours.

In specific embodiments, the glycosylase sensitive bases in the single primer PCR amplicons are uracil bases and the glycosylase is uracil DNA glycosylase (UDG). The UDG can be derived, for example, from *E. coli* or the marine bacterium BMTU 3346. The amount of UDG used to digest the uracil bases in the single primer PCR amplicons can range from about 0.001 units to about 20 units of enzyme. In some embodiments, about 10% v/v of a 1 unit/μL solution of UDG is contacted with the single primer PCR amplicons. The temperature of the digesting step can range from about 25° C. to about 45° C., or from about 35° C. to about 40° C. The duration of the digesting step can range from about 10 minutes to about 60 minutes.

In some embodiments, upon completion of the digesting step, the glycosylase can be inactivated by heat treatment at a temperature from about 85° C. to about 105° C. for about 1 minute to about 30 minutes.

In some embodiments glycosylase may be formulated with dual primer PCR reagents.

(ii) 5'-3' Exonucleases

In embodiments in which the single primer PCR amplicons comprise one or more nuclease resistant nucleotides near the 5' ends, the single primer PCR amplicons are contacted with a 5'-3' exonuclease. The 5'-3' exonuclease hydrolyzes and removes nucleotides from the 5' end of the amplicons until a nuclease resistant nucleotide is encountered. Thus, nucleotides at the 5' ends of the single primer PCR amplicons are removed, resulting in weakened base pairing between the 5' and 3' ends of the amplicons (see FIG. 5). Non-limiting specific examples of nuclease resistant primers are illustrated in FIG. 8.

Non-limiting examples of suitable 5'-3' exonucleases include bacteriophage T7 exonuclease, bacteriophage T5 exonuclease, bacteriophage lambda exonuclease, bacterial exonuclease VIII, or bacterial DNA polymerase I. The 5'-3' exonuclease can be wild type or modified such that a property (e.g., stability, specificity, kinetics) of the enzyme is altered.

The amount of 5'-3' exonuclease contacted with the single primer PCR amplicons can and will vary depending upon, e.g., the identity of the exonuclease, the number of ampli-cons, and the like. In general, the amount of 5' to 3' exonuclease that is contacted with the single primer PCR amplicons can range from about 0.01 to about 20 units of enzyme. The temperature of the exonuclease digesting step can range from about 25° C. to about 45° C., or from about 35° C. to about 40° C. The duration of the digesting step can range from about 10 minutes to about 60 minutes.

In some embodiments, upon completion of the digesting step, the 5' to 3' exonuclease can be inactivated by heat treatment at a temperature from about 75° C. to about 100° C. for about 1 minute to about 30 minutes.

Step V: Affixing Sequence Adapters

The next step following digestion comprises affixing adapters to the 5' ends of the amplified library of DNA products. The base paring at the ends of the amplified cDNA products are weakened because of digestion and the 3' end of each product contains sequence that is complementary to the adapter. Thus, the adapter primer is able to penetrate and effectively anneal to the DNA product. The adapters can be affixed to the DNA products during a polymerase chain reaction. Only structures with paired adapter sequences at each end will amplify efficiently.

At the end of the process the excess amplification primers and adapters can be removed by electrophoresis, chromatography, bead-based cleanup, or other standard nucleic acid purification methods.

The amplified cDNA library comprising the adapters can be entered in to a variety of applications including high throughput sequencing procedures including next generation sequencing, directional deep sequencing, Illumina® sequencing, 454 sequencing, ion torrent sequencing, SOLiD sequencing, nanopore sequencing, single molecule read time sequencing, and the like. The amplified DNA library can also be used in other well-known PCR and microarray based applications. (See PCR2 steps in FIGS. 14, 15, and 16).

(i) Dual Primer PCR Primers

The digested amplicons, detailed above in Step IV, are converted to dual primer PCR amplicons by contact with dual primer PCR primers under amplification conditions. The dual primer PCR primers comprise a forward or sense primer and a reverse or antisense primer. In general, a 3' portion of the dual primer PCR primers is homologous with the nested portion of the synthesis primers. The 3' portions that are homologous in the nest portion of the synthesis primer and the dual primer PCR primers can range in length from about 5, 6, 7, 8, 9, 10, 11, 12, 13, 14, 15, 16, 17, 18, 19, or 20 nucleotides. In specific embodiments, the 3' portions that are homologous in nest and the dual primer PCR primers can range in length from about 10 to about 16 nucleotides.

The total length of the dual primers can range from about 14 nucleotides to about 100 nucleotides. In some embodiments, the dual primers can range from about 18 to about 100 nucleotides in length. In other embodiments, the total dual primers can range from about 60 to about 80 nucleotides in length.

In general, the dual primer PCR primers are single-stranded and have a hydroxyl group at the 3' end for priming DNA synthesis. The amplification primers can comprise deoxyribonucleotides, ribonucleotides, or combinations thereof. The nucleotides can be standard nucleotides (i.e., adenosine, guanosine, cytidine, thymidine/uridine) or nucleotide analogs. A nucleotide analog refers to a nucleotide having a modified purine or pyrimidine base and/or a modified ribose moiety. A nucleotide analog can be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

In general, the dual PCR primer will have an average GC content of about 40-60%, and an average melting temperature ($T_m$) of about 50° C. to about 85° C. In certain embodiments, the single primer PCR primer can have a $T_m$ of about 50° C., about 55° C., about 60° C., about 65° C., about 70° C., or about 75° C.

(ii) Amplification Conditions

The digested single primer PCR amplicons are amplified via dual primer PCR to form the dual primer PCR amplicons. The amplification conditions provide at least two cycles with annealing temperatures and times to allow dual primer priming. Subsequent cycle annealing need only be sufficient for dual primer priming. A non-limiting example using long dual primers includes two cycles of denaturation (94'C/15 seconds), annealing (60° C./5 minutes), extension (70° C./1 minute) followed by 6 to 10 cycles of denaturation (94'C/15 seconds), annealing/extension (70° C./1 minute).

The weakened or nonexistent base pairing between the 5' digested ends and the 3' ends of the digested amplicons favors annealing of the dual primers to the digested amplicons. Thus, the dual primers are extended and the amplicons are replicated except for the 5' digested ends. Exponentially amplifiable template results after two amplification cycles. In certain embodiments these cycles will have lower annealing temperatures than exponential amplification cycles. Additional rounds of amplification result in the formation of dual primer PCR amplicons.

The dual primer PCR amplicons can be used directly in subsequent reactions or downstream applications without any intervening purification steps. Alternatively, the dual primer PCR amplicons can be purified from nucleotides, amplification primers, enzymes, and salts using well-known nucleic acid purification methods (e.g., PCR purification kits, etc.).

The dual primer PCR amplicons are dual primer due to inefficient amplification of single primer aducts formed during single to dual primer amplicon priming (see FIGS. 10 and 11).

(II) Switching Between Single Primer PCR Primers

Another aspect of the present disclosure provides a method for switching between at least two different single primer PCR primers. The method essentially comprises repeating steps in FIGS. 4 and 5, wherein a different single primer PCR primer replaces the dual PCR primers. In particular, the method comprises preparing a first set of single primer PCR amplicons by contacting a target nucleic acid with a first single primer PCR primer comprising a digestible 5' portion under amplification conditions, and treating the first set of single primer PCR amplicons with an enzyme capable of digesting a 5' portion of the first set of single primer PCR amplicons to form a first set of digested amplicons. The method further comprises contacting the first set of digested amplicons with a second single primer PCR primer comprising an optionally digestible 5' portion under amplification conditions to form a second set of single primer PCR amplicons. In certain embodiments the second set of single primer PCR amplicons may be treated with an enzyme capable of digesting a 5' portion of the second single primer PCR amplicons to form a second set of digested amplicons. In some embodiments, the second set of digested amplicon can be contacted with dual primer PCR primers as detailed above.

(III) Applications

The methods disclosed herein can be used during DNA amplification, wherein the DNA can be chromosomal, mitochondrial, plasmid, or cytoplasmic. The methods can also be used during RNA amplification, wherein the amplification can be directional or non-directional and the RNA can be coding or noncoding.

The single primer PCR amplicons and/or the dual primer PCR amplicons can be used in a variety of downstream applications. In some embodiments, the single or dual primer PCR amplicons can be sequenced using a next generation sequencing (NGS) platform. Non-limiting examples of NGS platforms include ion torrent sequencing, SOLiD sequencing, Illumina® sequencing, genome analyzer sequencing, 454 sequencing, directional deep sequencing, nanopore sequencing, single molecule read time sequencing, and the like. NGS technologies include clinical diagnostics, cancer diagnostics, molecular diagnostic tests, cancer therapeutics, drug development, microbiome technologies, food and agricultural technologies, and basic research.

In other embodiments, the single or dual primer PCR amplicons can be subjected to PCR-based screening/detection methods, qPCR, multiplex PCR, high throughput assays, microarray-based technologies, CHIP-based assays, comparative genomic hybridization, SNP genotyping, RFLP analyses, and the like for diagnostic, therapeutic, pharmaceutical, industrial, forensic, agricultural, and research purposes.

(IV) Kits

Still another aspect of the present disclosure provides kits for carrying out the methods described above. In some embodiments, the kit comprises single primer PCR primers and a corresponding enzyme (i.e., glycosylase or 5'-3' exonuclease) for digesting the resultant single primer PCR amplicons. In some embodiments, the kit can further comprise dual primer PCR primers. In other embodiments, the kit can comprise the dual primer PCR, the corresponding enzyme, and, optionally, the adapter sequences. The kits can further comprise suitable reaction buffers and/or a DNA polymerase suitable for PCR and deoxyribonucleotides.

Still another aspect of the present disclosure provides kits comprising the oligonucleotides described above, or kits for amplifying RNA using the processes detailed above.

In some embodiments, the kits can comprise (a) a plurality of synthesis primers in which each first synthesis primer comprises (5' to 3') a fixed 5' sequence optionally comprising at least one dU residue, a nested sequence having complementary to an adapter sequence, an optional internal tag sequence, and a random, semi-random or pool of specific 3' sequences, and (b) at least one amplification primer comprising the fixed 5' sequence comprising at least one dU residue and optionally the nested sequence having complementary to an adapter sequence.

In some embodiments, the kits can comprise (a) a plurality of first synthesis primers in which each first synthesis primer comprises (5' to 3') a fixed 5' sequence comprising at least one dU residue, a nested sequence having complementary to an adapter sequence, an optional internal tag sequence comprising a first tag sequence, and a random, semi-random or pool of specific 3' sequences, (b) a plurality of second synthesis primers in which each second synthesis primer comprises (5' to 3') a fixed 5' sequence comprising at least one dU residue, a nested sequence having complementarity to an adapter sequence, an optional internal tag sequence comprising a second tag sequence, and a random, semi-random or pool of specific 3' sequence, provided that either one or both of the pluralities of first and second synthesis primers comprises the first and/or second tag sequence, and (c) at least one amplification primer comprising the fixed 5' sequence comprising at least one dU residue and optionally the nested sequence having complementary to an adapter sequence.

The kits can further comprise a strand displacing polymerase, a 3'-5' deoxyribonuclease, a non-strand-displacing DNA polymerase, a thermophilic DNA polymerase, a uracil DNA Glycosylase, and/or Actinomycin D. In some embodiments, the kit can further comprise sequencing adapters.

The kits can further comprise a reverse transcriptase, a 3'-5', a non-strand-displacing DNA polymerase, a thermophilic DNA polymerase, a uracil DNA glycosylase, and/or Actinomycin D. In some embodiments, the kit can further comprise sequencing adapters.

Any of the kits can further comprise deoxyribonucleotides and one or more suitable buffers (e.g., a reverse transcriptase buffer, a second strand synthesis buffer, a thermocycling buffer, and the like).

The kits provided herein generally include instructions for carrying out the processes detailed above. Instructions included in the kits may be affixed to packaging material, may be included as a package insert or as a downloadable file. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

As various changes could be made in the above-described processes and kits without departing from the scope of the invention, it is intended that all matter contained in the above description and in the examples given below, shall be interpreted as illustrative and not in a limiting sense.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

A degenerate nucleotide can have 2-fold degeneracy (i.e., it can be one of two nucleotides), 3-fold degeneracy (i.e., it can be one of three nucleotides), or 4-fold degeneracy (i.e., it can be one of four nucleotides. A or C or G or T). Nucleotides having 3-fold degeneracy include "B" (can be C or G or T), "D" (can be A or G or T), "H" (can be A or C or T), and "V" (can be A or C or G). Nucleotides having 2-fold degeneracy include "K" (can be G or T), "M" (can be A or C), "R" (can be A or G), "Y" (can be C or T), "S" (can be C or G), and "W" (can be A or T).

As used herein, the terms "complementary" or "complementarity" refer to the association of double-stranded nucleic acids by base pairing through specific hydrogen bonds. The base paring may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some of the base pairs are complementary. The bases that are not complementary are "mismatched." Complementarity may also be complete (i.e., 100%), if all the base pairs of the duplex region are complementary.

As used herein, the term "homologous" refers to the extent two or more sequences are identical. Two sequences are considered to be homologous if they will hybridize to the same sequence under a defined set of conditions. Defined conditions include but are not limited to buffer formulation, temperature and sequence concentration.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) may be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm may be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs may be found on the GenBank website.

EXAMPLES

The following examples illustrate certain aspects of the invention.

Example 1: Whole Genome Amplification—Single to Dual Primer Switching

Human Genomic DNA (10 ng) was amplified using a semi-degenerate library primer (5'-UGGUUGU-GUUUGCTCTTCCGATCTKNNNKNKNK-3'; SEQ ID NO:1) and a WGA primer (5'-UGGUUGU-GUUUGCTCTTCCGATCT-3' (SEQ ID NO:2) using an enhanced DNA amplification kit (SeqPlex™; Sigma-Aldrich). The single primer amplicons were incubated in the absence or presence of 10% v/v of uracil DNA glycosylase (UDG) for 30 min at 37° C. The +/−digested amplicons were amplified in real time (i.e., monitored by the fluorescent dye, SYBR Green) using forward primer (5'-TCA-GACGTGTGCTCTTCCGATCT-3'; SEQ ID NO:3) and reverse primer (5'CCTACACGACGCTCTTCCGATCT-3'; SEQ ID NO:4) for two cycles at 94° C./30 sec, 50° C./10 min and then x cycles of 94° C./30 sec, 70° C./1 min, wherein x is the number of cycles to SYBR Green plateau. A Bioanalyzer trace of the dual primer PCR amplification is presented in FIG. 9. Dual primer PCR amplicons having an average size of about 150-250 bp were detected after single primer amplicons treated with UDG. Low yield of much larger products were detected without UDG treatment.

Example 2: Whole Genome Amplification—Primer Combinations

Genomic DNA was amplified and the resultant amplicons were treated with UDG as described above in Example 1. The digested amplicons were amplified in real time (i.e., monitored by fluorescent dye) using single or dual combinations of the single WGA, forward, and/or reverse primers from Example 1. A Bioanalyzer trace and the threshold cycle (Ct) values for each combination are shown in FIG. 11. The Ct values of the dual forward/reverse combination were about 8-9 cycles lower than either of these primers alone, indicating that <1% of the amplification products have complementary 5'-3' ends (i.e., 2-(8 to 9)<0.01). (See also FIG. 8). Additionally, there was a difference in product size distribution between the single and dual primer combinations.

Example 3A: Whole Genome Amplification—Short Vs. Long Dual Primers

Genomic DNA was amplified and the resultant amplicons were treated with UDG as described above in Example 1. The digested amplicons were amplified in real time (i.e., monitored by fluorescent dye) using the forward and reverse (short) PCR primers described above in Example 1 or using forward 5'-AATGATACGGCGACCACCGAGATCTA-CACTATAGCCTACACTCTTTCCCTACACGA CGCTCTTCCGATCT-3'; SEQ IS NO:5) and reverse (5'-CAAGCAGAAGACGGCATACGAGATAT-TACTCGGTGACTGGAGTTCAGACGTGTGC TCTTCC-GATCT-3'; SEQ ID NO:6) (long) PCR primers as described above (see FIG. 7). The results are presented in FIG. 12. The average length of the amplicons generated using the short dual primers was about 200 bp and the average length of the amplicons generated using the long dual primers was about 275 bp.

Example 3B: Whole Genome Amplification—Single Cell

The genome was amplified from a single human cell by 22 cycles of WGA followed by digestion with UDG as described above in Example 1. The digested amplicons were amplified for 9 cycles using the dual primers described in Example 1. As shown in FIG. 13, the single primer to dual primer method disclosed herein can be used to amplify very small quantities of nucleic acids.

Example 4: Directional Amplification of RNA

Universal human reference (UHR) RNA was amplified using the process essentially as detailed above (and outlined in FIG. 16). The pluralities of first and second synthesis primers used in the process are shown below in Table 1 (the nested sequence is italicized and the internal tag sequence is underlined).

TABLE 1

Examples of First and Second Synthesis Primers

| Type | Sequence (5' to 3') | SEQ ID NO: |
|---|---|---|
| 1st | GGUUGUGUUUG*CTCTTCCGATCT*<u>CTAACTAC</u>KNNNKNKNK | 7 |
| 1st | GGUUGUGUUUG*CTCTTCCGATCT*<u>CTAACTAC</u>NNNKNKKNK | 8 |
| 1st | GGUUGUGUUUG*CTCTTCCGATCT*<u>CTAACTAC</u>NKNNKNNKK | 9 |
| 1st | GGUUGUGUUUG*CTCTTCCGATCT*<u>CTAACTAC</u>TTTTTTTTT TTTTTVN | 10 |
| 2nd | GGUUGUGUUUG*CTCTTCCGATCT*<u>AAGCCTCG</u>TKNNNKNKNK | 11 |
| 2nd | GGUUGUGUUUG*CTCTTCCGATCT*<u>AAGCCTCG</u>TNNNKNKKNK | 12 |

TABLE 1-continued

Examples of First and Second Synthesis Primers

| Type | Sequence (5' to 3') | SEQ ID NO: |
|---|---|---|
| 2$^{nd}$ | GGUUGUGUUUGCTCTTCCGATCTAAGCCTCGTNKNNKNNKK | 13 |
| 2$^{nd}$ | GGUUGUGUUUGCTCTTCCGATCTAAGCCTCGTTTTTTTTTTTTTTTVN | 14 |

Amplification was performed in triplicate by real-time PCR using (1) a single primer having no barcode sequence, and (2) multiple primer types comprising two or more nucleotides of the upstream or downstream tag sequence (barcode). Examples of amplification primers are shown in Table 2 (the barcode or tag sequence is underlined).

TABLE 2

Examples of Amplification Primers

| Type | Sequence (5' to 3') | SEQ ID NO: |
|---|---|---|
| Single | GGUUGUGUUUGCTCTTCCGATCT | 15 |
| Multiple 1 | GGUUGUGUUUGCTCTTCCGATCTCTAAC | 16 |
| Multiple 2 | GGUUGUGUUUGCTCTTCCGATCTGAT | 17 |
| Multiple 3 | GGUUGUGUUUGCTCTTCCGATCTAGC | 18 |
| Multiple 4 | GGUUGUGUUUGCTCTTCCGATCTTC | 19 |

Amplification was monitored and manually stopped at cycle plateau. No significant difference was observed between the two amplification primer types. The results are shown in Table 3. Amplification performed with four barcode-specific primers, shows a ΔC(t) of ~6.5-6.9 for 1st-strand synthesis background, and 9.6-10 for 2nd-strand synthesis background. Quantitative percent background can be discerned by paired-end sequencing.

TABLE 3

Amplification with Single vs. Multiple Primers

| Primers | Single | Multi |
|---|---|---|
| | Downstream ΔC(t) | |
| Dn1,2-Up/Dn1,2 | 6.48 | 6.87 |
| Dn1-Up/Dn1,2 | 20.42 | 23.78 |
| Dn2-Up/Dn1,2 | 18.81 | 21.42 |
| | Upstream ΔC(t) | |
| Up1,2-Up/Dn1,2 | 10.08 | 9.64 |
| Up1-Up/Dn1,2 | 31.69 | 29.88 |
| Up2-Up/Dn1,2 | 13.53 | 14.82 |

Amplification product, following GenElute PCR Cleanup, appeared to be virtually free of primers, primer-dimers, adapters, and adapter-dimers. Amplification product (minus 122 bp Illumina® adapter sequence) ranges from ~80 to 180 base pairs, with yields of 10 to 12 micrograms per reaction.

What is claimed is:

1. A method for converting a single primer PCR amplicon to a dual primer PCR amplicon, the method comprising:
   treating the single primer PCR amplicon with an enzyme capable of digesting a 5' portion of the single primer PCR amplicon to form a digested amplicon, wherein the single primer PCR amplicon comprises at least one nuclease resistant nucleotide within about 5 nucleotides to about 25 nucleotides from its 5' end; and
   amplifying the digested amplicon with a pair of primers having homology to an undigested portion of the digested amplicon, thereby forming the dual primer PCR amplicon.

2. The method of claim 1, wherein the single primer PCR amplicon is generated by contacting a nucleic acid with a single PCR primer under amplification conditions, and the single PCR primer comprises a digestible 5' portion.

3. The method of claim 2, wherein the single PCR primer comprises at least one nuclease resistant nucleotide in the non-digestible 3' portion or at an interface between the digestible 5' portion and the non-digestible 3' portion, and the at least one nuclease resistant nucleotide comprises a 3'-5' phosphorothioate linkage, a 3'-5' phosphoborane linkage, a 2'-5' phosphodiester linkage, a 2' O-methyl moiety, a 2' fluoro moiety, a propyne base analog, or combination thereof.

4. The method of claim 1, wherein the single primer PCR amplicon is derived from RNA or DNA.

5. The method of claim 1, wherein the enzyme is a glycosylase.

6. The method of claim 5, wherein the glycosylase is a uracil DNA glycosylase, a thymine DNA glycosylase, a thymine glycol DNA glycosylase, an 8-oxoguanine DNA glycosylase, a 3-methylpurine DNA glycosylase, a Nth DNA glycosylase, a Nei DNA glycosylase, a MutY/Mig DNA glycosylase, or an alkyladenine-DNA glycosylase.

7. The method of claim 1, wherein the 5' portion of the single primer PCR amplicon comprises at least one glycosylase sensitive base.

8. The method of claim 7, wherein the at least one glycosylase sensitive base is uracil, carboxylcytosine, 2,6-diamino-4-hydroxy-5-formamidopyrimidine (FapyG), 4,6-diamino-5-formamidopyrimidine (FapyA), formyluracil, hydroxyuracil, hydroxycytosine, hydroxymethyl uracil, hypoxanthine, 3-methyladenine, 8-oxoguanine, 8-oxoadenine, thymine glycol, urea, or xanthine.

9. The method of claim 8, wherein the enzyme is uracil DNA glycosylase and the at least one glycosylase sensitive base is uracil.

10. The method of claim 1, wherein the enzyme is a 5'-3' exonuclease.

11. The method of claim 10 wherein the 5'-3' exonuclease is bacteriophage T7 exonuclease, bacteriophage T5 exonuclease, bacteriophage lambda exonuclease, bacterial exonuclease VIII, or bacterial DNA polymerase I.

12. The method of claim 1, wherein the at least one nuclease resistant nucleotide comprises a 3'-5' phosphorothioate linkage, a 3'-5' phosphoborane linkage, a 2'-5' phosphodiester linkage, a 2' O-methyl moiety, a 2' fluoro moiety, a propyne base analog, or combination thereof.

13. The method of claim 12, wherein the digestible 5' portion of the single PCR primer comprises at least one glycosylase sensitive base chosen from uracil, carboxylcytosine, 2,6-diamino-4-hydroxy-5-formamidopyrimidine (FapyG), 4,6-diamino-5-formamidopyrimidine (FapyA), formyluracil, hydroxyuracil, hydroxycytosine, hydroxymethyl uracil, hypoxanthine, 3-methyladenine, 8-oxoguanine, 8-oxoadenine, thymine glycol, urea, or xanthine.

14. The method of claim 1 wherein the single primer amplicon has been prepared beginning with RNA, the steps comprising:
   reverse transcribing at least one RNA molecule in the presence of a plurality of synthesis primers to generate a plurality of first and second strands of complementary DNA (cDNA), each of the synthesis primers comprising (5' to 3') a 5' sequence, wherein the 5' sequence is optionally digestible, a nested sequence having homology to an adapter primer sequence, an optional internal tag sequence comprising a first tag sequence, and a 3' sequence having complementarity to a portion of the at least one RNA molecule or to a portion of a first strand cDNA obtained from the at least one RNA molecule;

amplifying the plurality of double-stranded cDNA products in the presence of one amplification primer to generate an amplified library of cDNA products, the one amplification primer comprising the 5' sequence of the pluralities of the synthesis primers;

digesting the amplified library of cDNA products with a nuclease or glycosylase; and amplifying the digested amplified library of cDNA products with a pair of primers each comprising an adapter sequence, thereby affixing the adapter sequence to each 5' end of the library of digested cDNA products to generate the library of amplified RNA.

15. The method of claim 14, wherein the reverse transcribing is conducted in the presence of a reverse transcriptase, deoxyribonucleotides and optionally a DNA polymerase.

16. The method of claim 1 wherein the single primer amplicon has been prepared to render directional amplicons, the steps comprising:

reverse transcribing at least one RNA molecule in the presence of a plurality of first synthesis primers to generate a plurality of first strands of complementary DNA (cDNA), each of the first synthesis primers comprising (5' to 3') a digestible 5' sequence, a nested sequence having homology to an adapter primer sequence, an optional internal tag sequence comprising a first tag sequence, and a 3' sequence having complementarity to a portion of the RNA molecule;

synthesizing a plurality of double-stranded cDNA products by contacting the plurality of first strands of cDNA with a plurality of second synthesis primers, each of the second synthesis primers comprising (5' to 3') a digestible 5' sequence, a nested sequence having homology to an adapter primer sequence, an optional internal tag sequence comprising a second tag sequence, and a 3' sequence having complementarity to a portion of the first strands of cDNA, provided that either one or both of the pluralities of first and second synthesis primers comprise the first and/or second tag sequence such that each double-stranded cDNA product is flanked by at least one of the first or second tag sequences;

amplifying the plurality of double-stranded cDNA products in the presence of one amplification primer to generate an amplified library of cDNA products, the one amplification primer comprising the 5' sequence and the nested sequence of the pluralities of first and second synthesis primers;

digesting the amplified library of cDNA products with a nuclease or glycosylase; and amplifying the digested amplified library of cDNA products with a pair of primers each comprising an adapter sequence, thereby affixing the adapter sequence to each 5' end of the library of digested cDNA products to generate the library of directionally amplified RNA.

17. The method of claim 16, wherein the reverse transcribing is conducted in the presence of a reverse transcriptase, deoxyribonucleotides, and optionally Actinomycin D.

18. The method of claim 17, wherein the synthesizing commences with heat denaturation of the plurality of first strands of cDNA in the presence of the plurality of second synthesis primers, and the synthesizing is conducted in the presence of a non-strand-displacing DNA polymerase and deoxyribonucleotides.

19. The method of claim 18, wherein the tag sequences are at least 6 nucleotides in length.

20. The method of claim 1, which is devoid of one or more purification steps.

* * * * *